(12) United States Patent
Duan et al.

(10) Patent No.: US 10,409,869 B2
(45) Date of Patent: Sep. 10, 2019

(54) (R)- AND (S)-1-(3-(3-N,N-DIMETHYLAMINO-CARBONYL)PHENOXYL-4-NITRO-PHENYL)-1-ETHYL-N,N'-BIS(ETHYLENE)PHOSPHORAMIDATE, COMPOSITIONS AND METHODS FOR THEIR USE AND PREPARATION

(71) Applicant: OBI Pharma, Inc., Taipei (TW)

(72) Inventors: Jian-Xin Duan, South San Francisco, CA (US); Yeyu Cao, South San Francisco, CA (US); Xiaohong Cai, South San Francisco, CA (US); Hailong Jiao, South San Francisco, CA (US); Jing Yuan Ma, South San Francisco, CA (US); Mark Matteucci, South San Francisco, CA (US)

(73) Assignee: OBI PHARMA, INC., Taipei (TW)

( * ) Notice: Subject to any disclaimer, the term of this patent is extended or adjusted under 35 U.S.C. 154(b) by 0 days.

(21) Appl. No.: 15/752,854

(22) PCT Filed: Nov. 15, 2016

(86) PCT No.: PCT/US2016/062114
§ 371 (c)(1),
(2) Date: Feb. 14, 2018

(87) PCT Pub. No.: WO2017/087428
PCT Pub. Date: May 26, 2017

(65) Prior Publication Data
US 2018/0258116 A1 Sep. 13, 2018

Related U.S. Application Data

(60) Provisional application No. 62/255,905, filed on Nov. 16, 2015, provisional application No. 62/324,259, filed on Apr. 18, 2016.

(51) Int. Cl.
C07D 203/22 (2006.01)
A61K 31/396 (2006.01)
G06F 16/951 (2019.01)
G06F 16/954 (2019.01)
G01N 29/02 (2006.01)
G01N 29/22 (2006.01)
G06F 3/0484 (2013.01)
G06F 17/22 (2006.01)
H03H 9/02 (2006.01)
H03H 9/10 (2006.01)
H03H 9/25 (2006.01)
(Continued)

(52) U.S. Cl.
CPC ............ *G06F 16/951* (2019.01); *A61P 35/00* (2018.01); *C07F 9/564* (2013.01); *G01N 29/022* (2013.01); *G01N 29/222* (2013.01); *G06F 3/04842* (2013.01); *G06F 16/954* (2019.01); *G06F 17/2235* (2013.01); *H03H 9/02622* (2013.01); *H03H 9/1092* (2013.01); *H03H 9/25* (2013.01); *C07B 2200/07* (2013.01); *G01N 2291/0255* (2013.01); *G01N 2291/0256* (2013.01); *G01N 2291/0423* (2013.01)

(58) Field of Classification Search
CPC ............................ C07D 203/22; A61K 31/396
USPC .............................................. 548/956; 514/83
See application file for complete search history.

(56) References Cited

U.S. PATENT DOCUMENTS

| 5,472,956 A | 12/1995 | Borch et al. |
| 6,482,953 B1 | 11/2002 | Kim et al. |
| 8,507,464 B2 | 8/2013 | Matteucci et al. |

(Continued)

FOREIGN PATENT DOCUMENTS

| CN | 102924507 A | 2/2013 |
| JP | 2018-513876 A | 5/2018 |

(Continued)

OTHER PUBLICATIONS

Guise, C.P. et al. (2014) "Bioreductive prodrugs as cancer therapeutics: targeting tumor hypoxia," Chinese Journal of Cancer 33(2):80-86.

(Continued)

*Primary Examiner* — Charanjit Aulakh
(74) *Attorney, Agent, or Firm* — Foley & Lardner LLP; Daniel R. Shelton

(57) ABSTRACT

Provided herein are optically active compounds of the formulae (ii); and (III) and pharmaceutical compositions thereof. Also provided herein are processes of making these compounds and resolving the racemic mixture or the enrichment of same with in one of its enantiomers to provide (R)- and (S)-1-(3-(3-N,N-dimethylaminocarbonyl)phenoxyl-4-nitrophenyl)-1-ethyl-N,N'-bis(ethylene)phosphoramidate, and methods of treating cancer comprising administering such compounds.

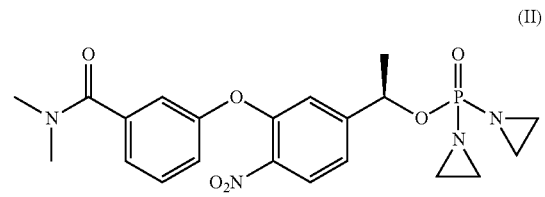

(II)

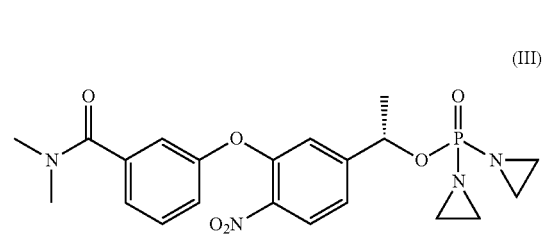

(III)

20 Claims, 14 Drawing Sheets

(51) Int. Cl.
A61P 35/00 (2006.01)
C07F 9/564 (2006.01)

(56) References Cited

U.S. PATENT DOCUMENTS

| | | |
|---|---|---|
| 2004/0214798 A1 | 10/2004 | Hu |
| 2008/0269268 A1 | 10/2008 | Schirok et al. |
| 2010/0256139 A1 | 10/2010 | Rockway et al. |
| 2011/0251159 A1 | 10/2011 | Matteucci et al. |
| 2014/0010805 A1 | 1/2014 | Hart et al. |
| 2014/0170240 A1 | 6/2014 | Matteucci et al. |
| 2018/0044360 A1 | 2/2018 | Duan et al. |

FOREIGN PATENT DOCUMENTS

| | | |
|---|---|---|
| WO | WO-2004/087075 | 10/2004 |
| WO | WO-2006/057946 A2 | 6/2006 |
| WO | WO-2007/002931 A2 | 1/2007 |
| WO | WO-2007/098089 A2 | 8/2007 |
| WO | WO-2008/083101 A1 | 7/2008 |
| WO | WO-2008/151253 A1 | 12/2008 |
| WO | WO-2009/018163 A1 | 2/2009 |
| WO | WO-2010/044686 | 4/2010 |
| WO | WO-2010/048330 A1 | 4/2010 |
| WO | WO-2011/066416 A1 | 6/2011 |
| WO | WO-2014/131023 | 8/2014 |
| WO | WO-2015/051921 A1 | 4/2015 |
| WO | WO-2016/145092 A1 | 9/2016 |
| WO | WO-2016/161342 A2 | 10/2016 |
| WO | WO-2016/210175 A1 | 12/2016 |

OTHER PUBLICATIONS

Jain, M. et al. (2004) "Sulfonyl-containing aldophosphamide analogues as novel anticancer prodrugs targeted against cyclophosphamide-resistant tumor cell lines," Journal of Medicinal Chemistry 47(15):3843-3852.
Mulcahy, R.T. et al. (1994) "Nitrobenzyl phosphorodiamidates as potential hypoxia-selective alkylating agents", Journal of Medicinal Chemistry 37:1610-1615.
International Search Report and Written Opinion (ISA/KR) for International Application No. PCT/US2016/062114, dated Mar. 9, 2017.
Chen, Y. et al., "Design of anticancer prodrugs for reductive activation", Medicinal Research Reviews, vol. 29, No. 1, 2009, pp. 29-64.
Communication pursuant to Rules 70(2) and 70a(2) EPC issued in EP 16815334.4 dated Jan. 8, 2019, 1 page.
Duan, J-X. et al. (2008) "Potent and Highly Selective Hypoxia-Activated Achiral Phosphoramidate Mustards as Anticancer Drugs," J. Med Chem 51:2412-2420.
Extended European search report issued in 16762438.6 dated Jul. 3, 2018, 10 pages.
Extended European Search Report issued in 16774352.5 dated Nov. 6, 2018, 11 pages.
Extended European Search Report issued in 16815334.4 dated Dec. 21, 2018, 7 pages.
Golub, T.R. et al. (1999) "Molecular Classification of Cancer: Class Discovery and Class Prediction by Gene Expression Monitoring," Science 286:531-537.
Hay et al. Substituent effects on the kinetics of reductively-initiated fragmentation of nitrobenzyl carbamates designed as triggers for bioreductive prodrugs, J. Chem. Soc., Perkin Trans. 1, 1999, 2759-2770. (Year:1999).
Hu et al., "Synthesis and structure-activity relationships of nitrobenzyl phosphoramide mustards as nitroreductase-activated prodrugs", Bioorganic & Medicinal Chemistry Letters 21 (2011) 3986-3991.
International Preliminary Report on Patentability issued in PCT/US2016/039092 dated Jan. 4, 2018, 9 pages.
K. Misiura et al., Stereospecific synthesis of chiral metabolites of Ifosfamide and their determination in the Urine, Journal of Medicinal Chemistry., vol. 26, 1983, pp. 674-679, XP002786859, US American Chemical Society. Washington. ISSN: 0022-2623.
Li, Z. et al., "Nitrobenzocyclophosphamides as Potential Prodrugs for Bioreductive Activation: Synthesis, Stability, Enzymatic Reduction, and Antiproliferative Activity in Cell Culture", Bioorganic & Medicinal Chemistry, vol. 11, No. 19, 2003, pp. 4171-4178.
NIH National Cancer Institute (2015) "Targeted Cancer Therapies Fact Sheet," see http://www.cancer.gov/about-cancer/treatment/types/targeted-therapies/targeted-therapies-fact-sheet, accessed Dec. 8, 2015.
Non-Final Office Action in U.S. Appl. No. 15/326,990, dated Apr. 30, 2018.
Non-Final Office Action in U.S. Appl. No. 15/557,053, dated Jun. 22, 2018.
Non-Final Office Action on U.S. Appl. No. 15/563,481 dated Nov. 16, 2018.
Non-Final Office Action on U.S. Appl. No. 15/736,285 dated Sep. 27, 2018.
Notice of Allowance in U.S. Appl. No. 15/326,990, dated Jul. 5, 2018.
Notice of Allowance on U.S. Appl. No. 15/326,990 dated Oct. 15, 2018.
Notice of Allowance on U.S. Appl. No. 15/557,053 dated Dec. 28, 2018.
Notice of Allowance on U.S. Appl. No. 15/736,285 dated Jan. 24, 2019.
Rastelli et al. Discovery of New Inhibitors of Aldose Reductase from Molecular Docking and Database Screening. Bioorganic & Medicinal Chemistry 10 (2002) 1437-1450. (Year: 2002).
Restriction Requirement in U.S. Appl. No. 15/563,481, dated Jul. 25, 2018.

(R)- AND (S)-1-(3-(3-N,N-DIMETHYLAMINO-CARBONYL)PHENOXYL-4-NITRO-PHENYL)-1-ETHYL-N,N'-BIS (ETHYLENE)PHOSPHORAMIDATE, COMPOSITIONS AND METHODS FOR THEIR USE AND PREPARATION

CROSS-REFERENCE TO RELATED APPLICATIONS

This application is a national stage application under 35 U.S.C. § 371 of International Application No. PCT/US2016/062114, filed Nov. 15, 2016, which in turn claims priority under 35 U.S.C. § 119(e) to U.S. Provisional Patent Application Nos. 62/255,905, filed Nov. 16, 2015, and 62/324,259, filed Apr. 18, 2016, the content of each of which is hereby incorporated by reference in its entirety.

FIELD OF INVENTION

The present invention provides optically active forms of the compound 1-(3-(3-N,N-dimethylaminocarbonyl)phenoxyl-4-nitrophenyl)-1-ethyl-N,N'-bis(ethylene)phosphoramidate suitable as therapeutic agents, pharmaceutical compositions of such compounds and methods of treating cancer, as well as a process for their resolution from, or enrichment in one of its enantiomers, of the racemic mixture of the compound (R,S)-1-(3-(3-N,N-dimethylaminocarbonyl)phenoxyl-4-nitrophenyl)-1-ethyl-N,N'-bis(ethylene) phosphoramidate, or stereoselective synthesize the optically pure (R) and (S)-1-(3-(3-N,N-dimethylaminocarbonyl)phenoxyl-4-nitrophenyl)-1-ethyl-N,N'-bis(ethylene)phosphoramidate.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment is a cause of adverse side effects in patients and can limit the amount of anti-cancer drug administered to a cancer patient.

Aldo-keto reductase family 1 member C3 (AKR1C3) is an enzyme that, in humans, is encoded by the AKR1C3 gene. This gene encodes a member of the aldo/keto reductase superfamily, which consists of more than 40 known enzymes and proteins. These enzymes catalyze the conversion of aldehydes and ketones to their corresponding alcohols by utilizing NADH and/or NADPH as cofactors.

Many cancer cells overexpress AKR1C3 reductase relative to normal cells (See e.g., Cancer Res. 2010; 70:1573-1584; Cancer Res. 2010; 66: 2815-2825). PR 104 has been shown

PR 104

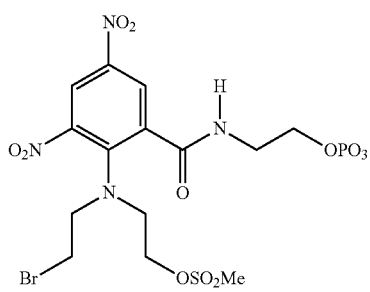

to be a weak substrate for AKR1C3 and was tested in clinical trials. This compound is not a selective AKR1C3 activated prodrug as it can also be activated under hypoxic conditions. PR 104 was ineffective in clinical trials.

Accordingly, there remains a need for compounds suitable for treating cancer patients, including for selective AKR1C3 reductase activated prodrugs for treating cancer patients. The present invention meets this need.

SUMMARY OF THE INVENTION

In one aspect, provided herein are compounds of formulae Ia and Ib:

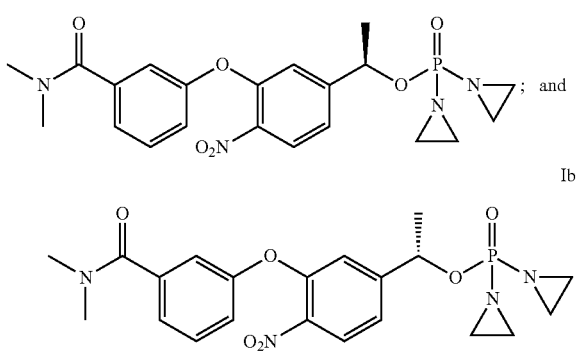

or an isotopic variant, solvate or hydrate thereof.

The compounds provided herein include individual enantiomers as well as enriched mixtures of enantiomers.

In another aspect, provided herein is a pharmaceutical composition comprising a compound provided herein and at least one pharmaceutically acceptable excipient. In another aspect, provided herein is a unit dose of the pharmaceutical composition provided herein.

In another aspect, provided herein is a method for treating cancer in a patient, comprising administering to the patient a therapeutically effective amount of a compound or a pharmaceutically acceptable composition as provided herein. In one embodiment, the cancer is one wherein AKR1C3 reductase levels are high or are higher than usual in such a cancer. In one embodiment, the cancer is liver cancer and more specifically, hepatocellular carcinoma (HCC). In one embodiment, the cancer is non-small cell lung cancer or melanoma. In one embodiment, the cancer is prostate cancer. In one embodiment, the cancer is breast cancer. In one embodiment, the cancer is a leukemia. In one embodiment, the cancer is esophagial cancer. In one embodiment, the cancer is renal, gastric, colon, brain, bladder, cervical, ovarian, head and neck, endometrial, pancreatic, a sarcoma, or rectal cancer. In a further aspect, the method comprises determining the AKR1C3 reductase level of the cancer by methods using an AKR1C3 antibody, and administering a therapeutically effective amount of a compound or a pharmaceutically acceptable composition provided herein to said patient if said level is equal to or greater than a predetermined value. In one aspect, the method comprises prior to administration, determining an intratumoral AKR1C3 reductase level in a sample isolated from the patient and selecting the patient for the therapy if the level is equal to or greater than a predetermined level. In some embodiments, a therapeutically effective amount of a cancer treatment other than a treatment comprising administration of a compound or a pharmaceutically acceptable composition provided herein is administered if the level does not exceed or is less than said predetermined value. Methods of determining the therapeutically effective amount, appropriate mode of administration of the compounds and compositions provided herein will be apparent to the skilled artisan upon reading this disclosure and based on other methods known to them. AKR1C3 levels are measured following routine methods well known to the skilled artisan.

DETAILED DESCRIPTION

Definitions

Figure 1A:
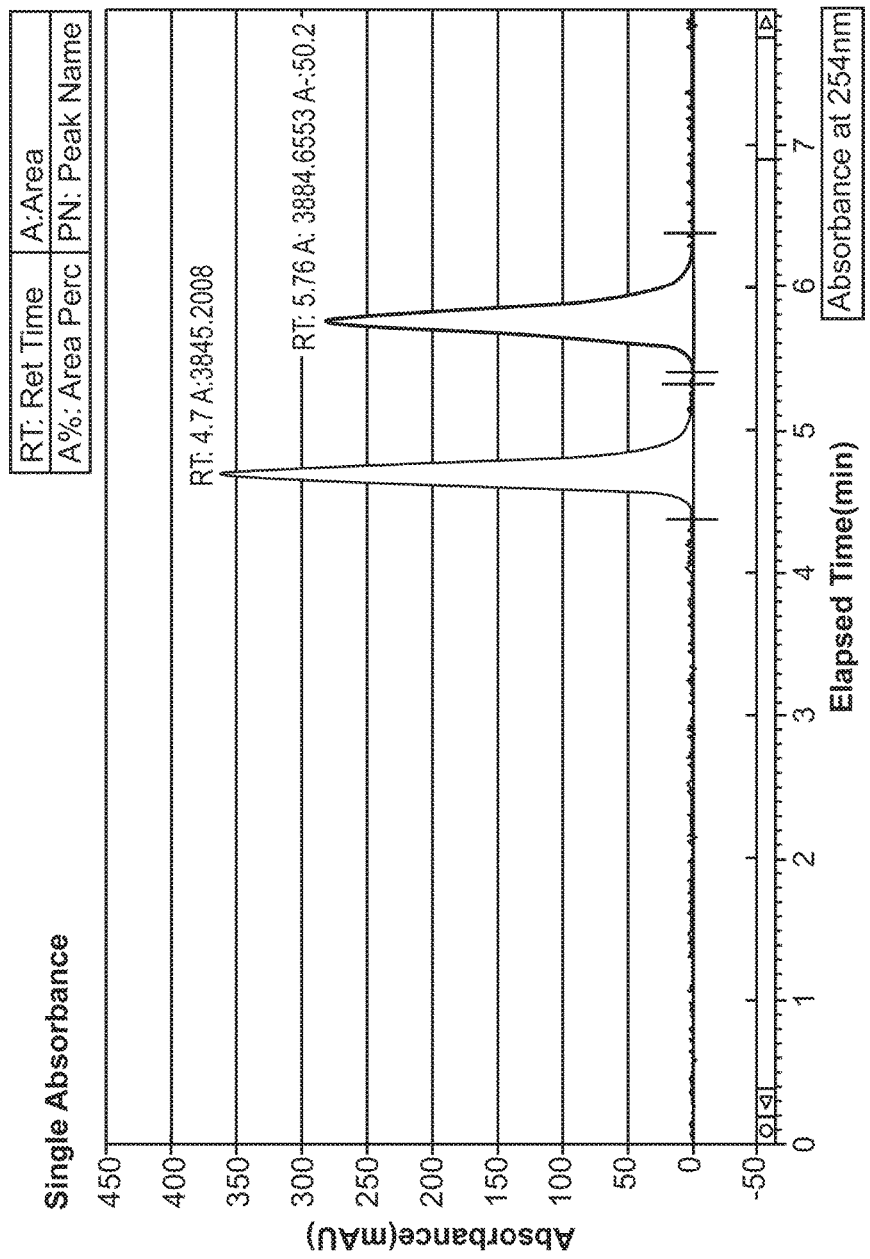
FIG. 1 depicts an LC chromatogram for the resolution of the two enantiomers of 1-(3-(3-N,N-dimethylaminocarbonyl)phenoxyl-4-nitrophenyl)-1-ethyl-N,N'-bis(ethylene) phosphoramidate by chiral high pressure liquid chromatography on a CHIRALPAK OZ-H 6×250 mm, 5 um (Daicel) chiral column eluting with 65/35 $CO_2$/methanol.

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about". Reagents described herein are exemplary and equivalents of such may be known in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"Leaving group" refers to a moiety that can be displaced under nucleophilic displacement conditions well known to the skilled artisan. Leaving groups include, without limitation halo and $-OSO_2-R^{20}$, where $R^{20}$ is optionally substituted alkyl, aryl, cycloalkyl, heterocyclyl, or heteroaryl.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Cancer" refers to leukemias, lymphomas, carcinomas, and other malignant tumors, including solid tumors, of potentially unlimited growth that can expand locally by invasion and systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The terms "optically active" and "enantiomerically active" refer to a collection of molecules, which has an enantiomeric excess of no less than about 10%, no less than about 20%, no less than about 30%, no less than about 40%, no less than about 50%, no less than about 60%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.8%, or no less than about 99.9%. In certain embodiments, the enantiomeric excess for an optically or enantiomerically active compound is no less than about 90%, no less than about 95%, no less than about 98%, or no less than about 99%.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The terms "optically pure" and "enantiomerically pure" refer to a collection of molecules, which has an enantiomeric excess (ee) of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.8%, or no less than about 99.9%. In certain embodiments, the enantiomeric excess for an optically or enantiomerically pure compound is no less than about 90%, no less than about 95%, no less than about 98%, or no less than about 99%. An enantiomeric excess of a compound can be determined by any standard methods used by one of ordinary skill in the art, including, but not limited to, chiroptical chromatography (gas chromatography, high-performance liquid chromatography, and thin-layer chromatography) using an optically active stationary phase, isotopic dilution, electrophoresis, calorimetry, polarimetry, NMR resolution methods with chiral derivatization, and NMR methods with a chiral solvating agent or chiral shift reagent.

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single stereoisomer of a compound, as determined by standard analytical methods.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$) carbon-12 ($^{12}C$), carbon-13 (13C), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^{2}H$, for example, or any carbon can be $^{13}C$, as example, or any nitrogen can be $^{15}N$, as example, and any oxygen can be $^{18}O$, where feasible according to the judgment of one of skill. In certain embodiments, an "isotopic variant" of a compound contains unnatural proportions of deuterium.

The phrase "an isotopic variant thereof; or pharmaceutically acceptable salt, solvate, hydrate, or prodrug thereof" has the same meaning as the phrase "an isotopic variant of the compound referenced therein; or a pharmaceutically acceptable salt, solvate, or prodrug of the compound referenced therein or an isotopic variant the compound referenced therein."

"Patient" and "subject" are used interchangeably to refer to a mammal in need of treatment for cancer. Generally, the patient is a human. Generally, the patient is a human diagnosed with cancer. In certain embodiments a "patient" or "subject" may refer to a non-human mammal used in screening, characterizing, and evaluating drugs and therapies, such as, a non-human primate, a dog, cat, rabbit, pig, mouse or a rat.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; and Pharmaceutical Preformulation and Formulation, 2nd ed.; Gibson Ed.; CRC Press LLC: Boca Raton, Fla., 2009.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Solid tumor" refers to solid tumors including, but not limited to, metastatic tumors in bone, brain, liver, lungs, lymph node, pancreas, prostate, skin and soft tissue (sarcoma).

The term "solvate" refers to a complex or aggregate formed by one or more molecules of a solute, e.g., a compound provided herein, and one or more molecules of a solvent, which is present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

"Therapeutically effective amount" of a drug refers to an amount of a drug that, when administered to a patient with cancer, will have the intended therapeutic effect, e.g., alleviation, amelioration, palliation or elimination of one or more manifestations of cancer in the patient. A therapeutic effect does not necessarily occur by administration of one dose, and may occur only after administration of a series of doses. Thus, a therapeutically effective amount may be administered in one or more administrations.

"Treating," "treatment of," or "therapy of" a condition or patient refers to taking steps to obtain beneficial or desired results, including clinical results. For purposes of this invention, beneficial or desired clinical results include, but are not limited to, alleviation or amelioration of one or more symptoms of cancer; diminishment of extent of disease; delay or slowing of disease progression; amelioration, palliation, or stabilization of the disease state; or other beneficial results. Treatment of cancer may, in some cases, result in partial response or stable disease.

"Tumor cells" refers to tumor cells of any appropriate species, e.g., mammalian such as murine, canine, feline, equine or human.

DESCRIPTIVE EMBODIMENTS

Provided herein are compounds of formulas Ia and Ib:

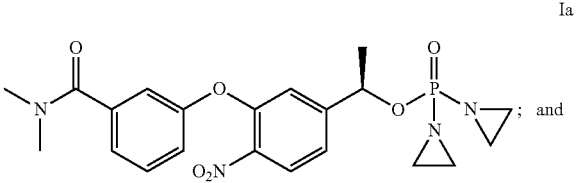

Ia

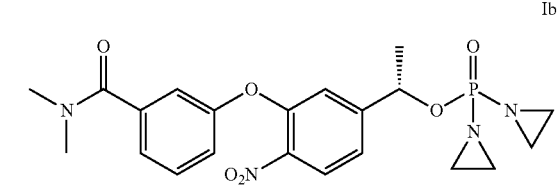 [SMILES: CC(OP(=O)(N1CC1)N1CC1)c1ccc([N+](=O)[O-])c(Oc2cccc(C(=O)N(C)C)c2)c1]

Ib or an isotopic variant, solvate or hydrate thereof.

In another aspect, provided herein is a process of preparing a compound of formula I:

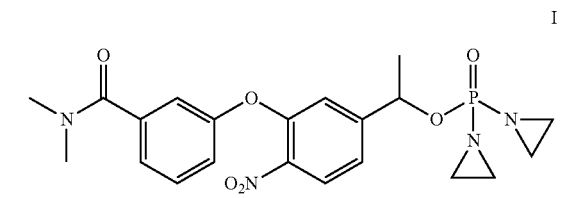

I comprising contacting a compound of formula II:

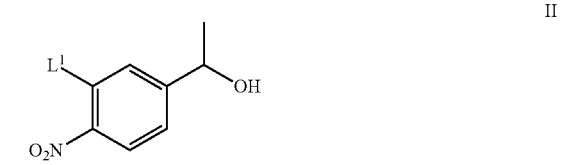

II with $POCl_3$ and $H_2NCH_2CH_2L^{2*}$, or a salt thereof, to provide a compound of formula III,

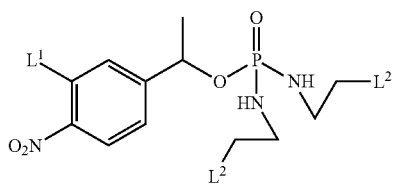

III wherein $L^1$ and $L^2$ independently are a leaving group, and the compound of formula III is then taken on to provide a compound of formula I.

Certain methods for synthesizing compounds provided herein are provided herein. Other methods for synthesizing these and other compounds provided herein will be apparent to the skilled artisan based on the adaptation of, and the replacement of reagents and reactants in, synthetic methods well known to them. See, e.g., Hay et al., *J. Med. Chem.* 2003, 46, 2456-2466 and Hu et al., Bioorganic & Medicinal Chemistry Letters 21 (2011) 3986-3991. Starting materials useful for preparing the compounds provided herein are commercially available or can be prepared following routine methods. The reactions are commonly carried out in an inert solvent and heated if necessary. The skilled artisan will readily appreciate that certain reactions may require the use of a protecting group. Protecting groups are well known to the skilled artisan and described, e.g., in Greene's Protective Groups in Organic Synthesis. Peter G. M. Wuts and Theodora W. Greene, 4$^{th}$ Edition or a later edition, John Wiley & Sons, Inc., 2007. The reaction products may be separated following routine methods such as crystallization, precipitation, distillation, and/or chromatography. The purity of a compound or an intermediate can be ascertained using well known methods such as $^1$H-NMR, HPLC, TLC, and the like.

In another embodiment, the present invention relates to a process for the optical resolution of a compound of formula I. In view of the pharmaceutical importance of the compounds of formula Ia and Ib of the present invention, it has been imperative to resolve the compound of formula I using an effective industrial process and, especially, in a good yield and with excellent chemical and enantiomeric purity.

The Applicant has developed a process for the optical resolution of the compound of formula I, which makes it possible to obtain the compound of formulae Ia and Ib with good characteristics of yield and chemical and enantiomeric purity. The process of the invention makes it possible to obtain either enantiomer of the compound of formula I in an excellent enantiomeric excess, with high productivity and in an excellent yield whilst economizing on the solvents used. More specifically, the present invention relates to a process for the optical resolution of a compound of formula I:

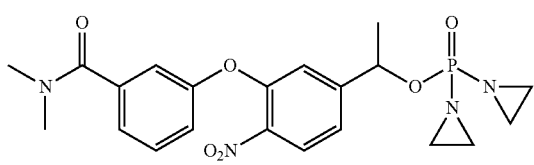

I to yield its enantiomers of absolute configuration (R) and (S), respectively of formulae (Ia) and (Ib):

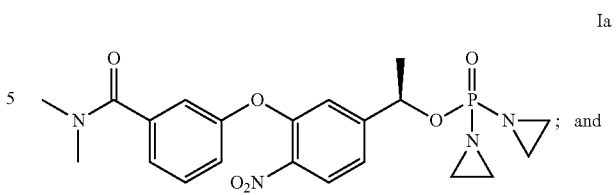

wherein a racemic or enantiomerically enriched mixture of the compound of formula I is separated into its two enantiomers, (R)-1-(3-(3-N,N-dimethylaminocarbonyl)phenoxyl-4-nitrophenyl)-1-ethyl-N,N'-bis(ethylene)phosphoramidate of formula (Ia) and (S)-1-(3-(3-N,N-dimethylaminocarbonyl)phenoxyl-4-nitrophenyl)-1-ethyl-N,N'-bis(ethylene)phosphoramidate of formula (Ib), by chiral chromatography.

Optical resolution is understood to mean the separation of the two enantiomers of a racemic mixture or of any mixture of those two enantiomers.

A racemic mixture is understood to mean a mixture of two enantiomers in a ratio of from 55:45 to 45:55, preferably in a ratio of 50:50.

An enantiomerically enriched mixture is understood to mean a mixture of two enantiomers containing significantly more of one of the enantiomers in a ratio varying between 55:45 and 90:10.

Chiral chromatography is understood to mean the arrangement making possible the separation of the enantiomers of a mixture by means of a chiral stationary phase and a mobile phase composed of a solvent or of a mixture of solvents and gases.

In accordance with one of the embodiments of the invention, the stationary phase used for the chiral chromatography comprises a silica gel impregnated with a functionalized polysaccharide.

The mobile phase used for the chiral chromatography in one embodiment, comprises a mixture of an alcohol and an organic gas. Among the alcohols that may be used for the chiral chromatography there may be mentioned, without implying any limitation, isopropanol, ethanol and methanol. In one embodiment, the alcohol used for the chiral chromatography is methanol.

Among the organic gases that may be used for the chiral chromatography there may be mentioned, without implying any limitation, are organic gases that can be used at high pressure. An organic gas preferably used is $CO_2$. In one embodiment, the mobile phase used for the chiral chromatography comprises a mixture of methanol and $CO_2$. In one embodiment of the invention, the mobile phase used for the chiral chromatography comprises a mixture of methanol and $CO_2$ in a ratio varying from 50:50 to 2:98.

In one embodiment of the invention, the mobile phase used for the chiral chromatography is recycled. In one embodiment of the invention, the chiral chromatography is carried out at a temperature from 15° C. to 40° C. inclusive. In one embodiment of the invention, the optical resolution is carried out on a racemic mixture of 1:1 of formula (I). In one of embodiment of the invention, the (R)-enantiomer of 1-(3-(3-N,N-dimethylaminocarbonyl)phenoxyl-4-nitrophenyl)-1-ethyl-N,N'-bis(ethylene)phosphoramidate is used. In accordance with one of embodiment of the invention, the (S)-enantiomer of 1-(3-(3-N,N-dimethylaminocarbonyl) phenoxyl-4-nitrophenyl)-1-ethyl-N,N'-bis(ethylene)phosphoramidate is used.

In accordance with a one embodiment of the invention, a continuous multi-column separation process is used.

In accordance with another embodiment of the invention, a simulated moving bed chromatography process is used. Simulated moving bed chromatography is understood to mean a continuous chromatography process which makes it possible to simulate movement of the stationary phase in the opposite direction to the movement of the mobile phase. Such a process makes it possible to separate compounds that are difficult or impossible to separate by conventional chromatography techniques. When a chiral stationary phase is used, such a process is especially useful for the separation of enantiomers. Use of simulated moving bed chromatography makes it possible to carry out continuous resolution of a mixture of enantiomers with high productivity, whilst reducing the amounts of stationary and mobile phases used compared with discontinuous chromatography processes.

List of Abbreviations Used

DMF: Dimethylformamide
TEA: Triethylamine
RT: Room temperature
IPM: Isophosphoramide mustard
THF: tetrahydrofuran
DIAD: Diisopropyl azodicarboxylate The Examples hereinbelow illustrate the invention.

EXAMPLES

Example 1. Preparation of Compound TH 2870

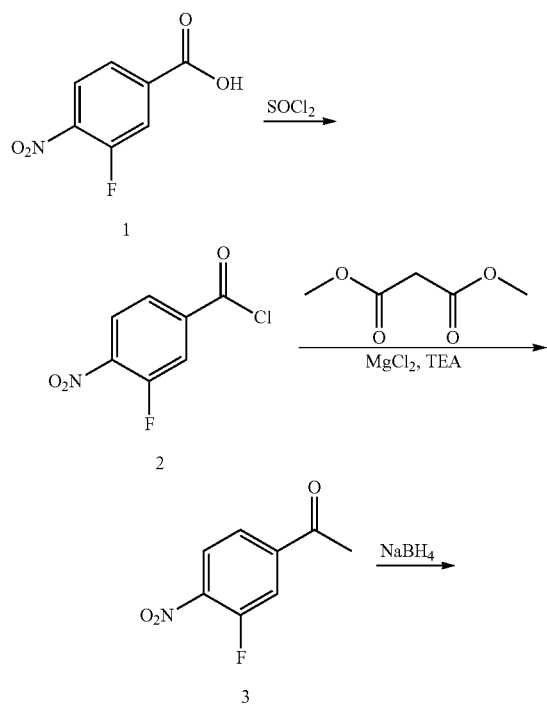

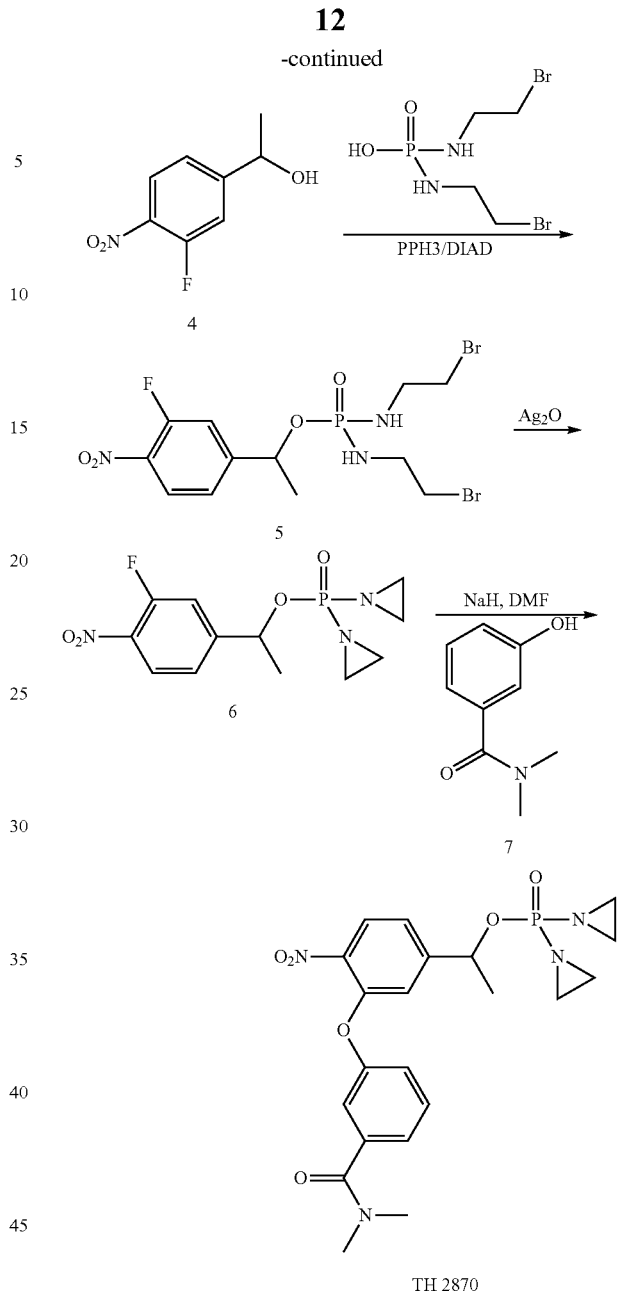

Compounds 2-6 were synthesized as described below.

a. Synthesis of Compound 3:

Compound 1 (3 g, 16.2 mmol) was refluxed in SOCl$_2$ (10 mL) with DMF (3 drops) for 3 h and then SOCl$_2$ was removed under vacuum. The residue was diluted with toluene (5 mL) and was used in the following step without further purification.

A mixture of MgCl$_2$ (930 mg, 9.8 mmol), TEA (4.7 mL, 33.4 mmol) and dimethyl malonate (1.9 mL, 16.6 mmol) was stirred at RT for 1.5 h followed by addition of the above mentioned toluene solution of Compound 2. The resulting mixture was stirred at RT for another 1.5 h then conc. HCl (4 mL) was added and stirred for 5 minutes. The mixture was extracted with EtOAc (30 mL×3), dried (Na$_2$SO$_4$), filtered and concentrated under reduced pressure. To the residue was added 6N HCl (30 mL and the mixture was refluxed overnight. The mixture was extracted with EtOAc (30 mL×3), dried (Na$_2$SO$_4$), filtered and concentrated under reduced pressure. The residue was purified via FCC (silica gel, EtOAc/Hexane) to afford Compound 3 as a light yellow solid (1.9 g, 63% yield).

$^1$H NMR (CDCl$_3$, 400 MHz) δ: 8.16 (d, J=8.0 Hz, 1H), 7.86 (t, d=9.2 Hz, 2H), 2.68 (s, 3H) ppm.

b. Synthesis of Compound 4

To a mixture of Compound 3 (1.9 g, 10.4 mmol) in MeOH (20 mL) at −10 C was added NaBH$_4$ (418 mg, 11 mmol) in portions. The mixture was stirred between −10 C to 0 C for 20 minutes, diluted with EtOAc (300 mL), washed with sat. NH$_4$Cl aqueous solution, brine, dried (Na$_2$SO$_4$). Filtered and concentrated under reduced pressure. The residue was purified via FCC (silica gel, EtOAc/Hexane) to afford Compound 4 as a light yellow oil (1.44 g, 75% yield).

$^1$H NMR (CDCl$_3$, 400 MHz) δ: 8.06 (t, J=8.4 Hz, 1H), 7.35 (d, J=11.6 Hz, 1H), 7.30 (d, J=11.6 Hz, 1H), 5.01-4.99 (m, 1H), 1.52 (d, J=6.4 Hz, 3H) ppm.

c. Synthesis of Compound 5

To a mixture of Compound 4 (1.44 g, 7.78 mmol), Br-IPM (2.88 g, 9.34 mmol), PPh$_3$ (3.06 g, 11.67 mmol) in THF (60 mL) at 0° C. was added DIAD (2.34 g, 11.67 mmol). The mixture was stirred at 0° C. for 1.5 h, concentrated under reduced pressure and purified via FCC (silica gel, EtOAc/Hexane) to afford Compound 5 as a light yellow oil (1.0 g, 27% yield).

$^1$H NMR (CDCl$_3$, 400 MHz) δ: 8.09 (t, J=8.0 Hz, 1H), 8.31 (dd, J=2.4, 13.6 Hz, 2H), 5.52-5.60 (m, 1H), 3.54-3.19 (m, 8H), 1.63 (d, J=6.4 Hz, 3H) ppm.

d. Synthesis of Compound 6

A mixture of Compound 5 (1 g, 2.1 mmol) and Ag$_2$O (3 g) in THF (50 mL) was stirred at 65° C. for 3 h. Filtered and concentrated under reduced pressure. The residue was purified via FCC (silica gel, Acetone/Hexane) to afford Compound 6 as a yellow solid (0.6 g, 90% yield).

$^1$HNMR (CDCl$_3$, 400 MHz) δ: 8.08 (t, J=8.0 Hz, 1H), 7.36 (d, J=11.6 Hz, 1H), 7.31 (d, J=8.4 Hz, 1H), 5.70-5.67 (m, 1H), 2.25-2.08 (m, 8H), 1.64 (d, J=6.4 Hz, 3H) ppm.

e. Preparation of Compound 7

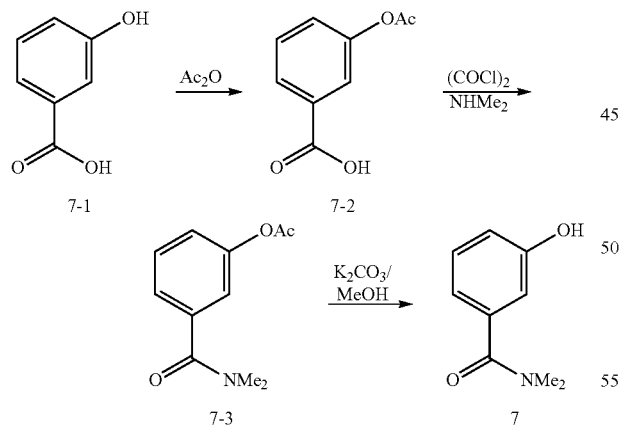

Preparation of Compound 7-2

Ac$_2$O (562 mL, 1.5 eq) was added drop wise to a solution of compound 7-1 (150 g, 1.08 mol) in Pyridine (700 mL) at 0° C., stirred at r.t. for 6 hrs. Evaporated, poured into ice water, filtered, the filter cake was dried to give compound 7-2 as a white solid (150 g, 74% yield).

$^1$H NMR (400 MHz, CDCl$_3$): δ ppm 8.00~7.98 (d, J=7.6 Hz, 1H), 8.03 (s, 1H), 7.83 (s, 1H), 7.51~7.47 (t, J=8.0 Hz, 1H), 7.36~7.34 (dd, J=8.0 Hz 1.2 Hz, 1H), 2.34 (s, 3H).

Preparation of Compound 7-3

To a solution of compound 7-2 (150 g, 833 mmol) in DCM (1500 mL), DMF (15 mL) was added, cooled to 0° C. followed by the addition of oxayl chloride (225 mL, 2.50 mol), stirred at r.t. for 4 hrs. Evaporated, the residue was dissolved in DCM (1000 mL) cooled to 0° C. followed by the addition of 2M solution of dimethylamine in THF (900 mL, 1.8 mol), stirred at r.t. for 20 hrs. Quenched with H$_2$O (1500 mL), extracted with DCM (2000 mL×3), evaporated to give crude compound 7-3 as a pale yellow liquid (137 g, 80% yield). $^1$H NMR (400 MHz, CDCl$_3$): δ ppm 7.43~7.39 (t, J=8.0 Hz, 1H), 7.29~7.28 (d, J=7.6 Hz, 1H), 7.17~7.13 (m, 2H), 3.00 (s, 6H), 2.32 (s, 3H).

Preparation of Compound 7

To a solution of compound 7-3 (137 g, 661 mmol) in MeOH (1000 mL), K$_2$CO$_3$ (276 g, 2 mol) was added, stirred at r.t. for 5 hrs. Filtered, the filtrate was evaporated. The residue was dissolved in H$_2$O (1000 mL), acidified by 4N HCl to PH6.0, filtered, the filter cake was dried to give compound 7 as a white solid (60 g, 55% yield).

$^1$H NMR (400 MHz, CDCl$_3$): δ ppm 8.25 (s, 1H), 7.19~7.15 (d, J=8.0 Hz, 1H), 6.96~6.95 (t, J=2.0 Hz, 1H), 6.84~6.81 (s, 2H), 3.11 (s, 3H), 2.96 (s, 3H).

f. Synthesis of TH 2870

To a mixture of compound 7 in DMF (60 mL) at 0° C. was added NaH (60%, 0.508 g, 12.7 mmol) in portions. The mixture was stirred at 0 C for 0.5 h before Compound 6 (2 g, 6.35 mmol) was added and then stirred at 0 C for 2.5 h. The mixture was diluted with EtOAc (500 mL), washed with brine (50 mL×3), dried over Na$_2$SO$_4$, filtered, concentrated under reduced pressure and purified via FCC (silica gel, Acetone/Hexane) to afford TH 2870 as a yellow oil.

Final Purification of TH 2870:

TH 2870 as mentioned above was purified via semi-prep HPLC (C18 column, acetonitrile/water). The combined collections were concentrated under reduced pressure to afford a light yellow oil as the final product. Acetonitrile was added to the evaporations as an azeotrope agent to remove water.

$^1$H NMR (400 MHz, CDCl$_3$): δ ppm 7.98~7.96 (d, J=8.4 Hz, 1H), 7.43~7.39 (m, 1H), 7.27~7.21 (m, 2H), 7.10~7.06 (m, 3H), 5.62~5.55 (m, 1H), 3.09 (s, 3H), 2.97 (s, 3H), 2.19~2.00 (m, 8H), 1.58~1.57 (d, J=6.4 Hz, 3H). MS: m/z 460.8[M+1]+. PLC: 254 nm: 94.8%.

Example 2. Alternative Preparation of Compound TH 2870

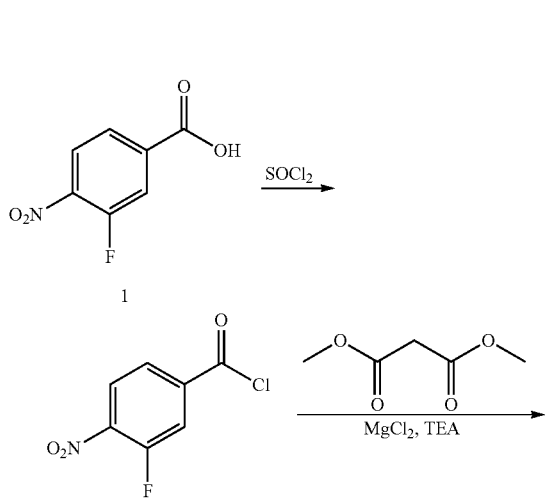

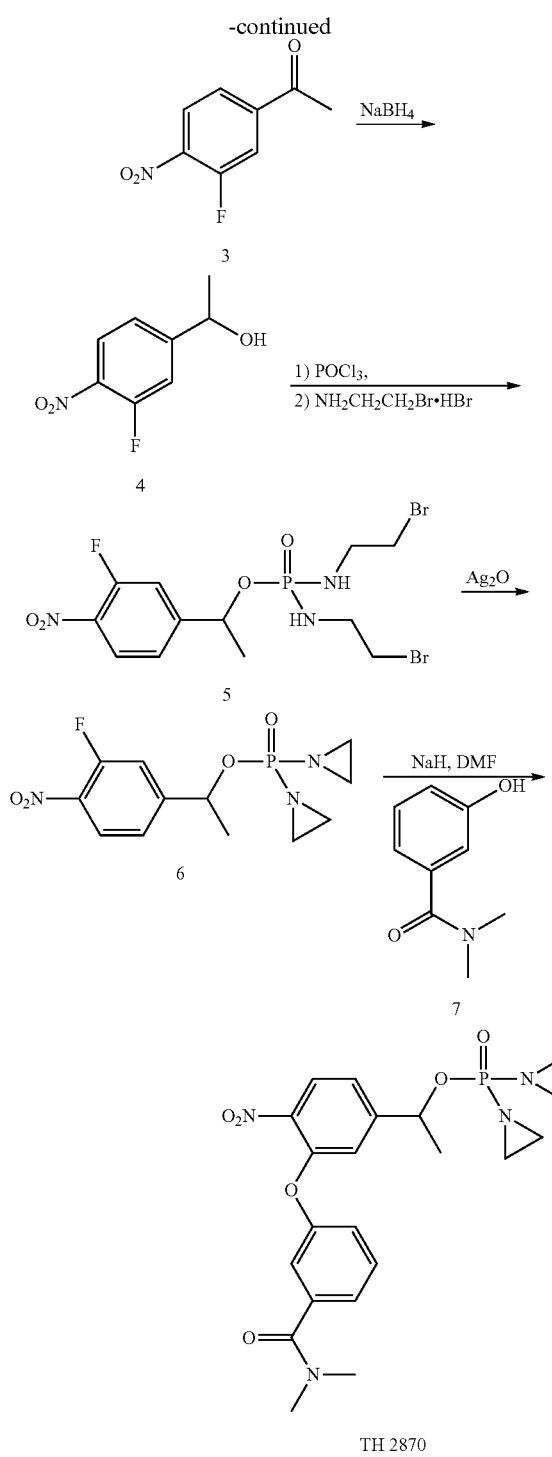

a. Preparation of Compound 3

Compound 1 (200 g, 1.08 mol) was refluxed in SOCl$_2$ (700 mL) with DMF (10 ml) for 3 hrs and then SOCl$_2$ was removed under vacuum. The residue was diluted with toluene (400 mL) and was used in the following step without further purification.

A mixture of MgCl$_2$ (103 g, 1.08 mol), TEA (500 mL, 3.60 mol) and dimethyl malonate (145 g, 1.1 mol) was stirred at RT for 1.5 hrs before the above mentioned toluene solution of compound 2 was added drop wise. The resulting mixture was stirred at RT for another 1.5 hrs. Washed with H$_2$O (2 L), extracted with EtOAc (2 L×5), evaporated, 4N HCl was added until PH6.0 and stirred for 5 minutes. The mixture was extracted with EtOAc (2 L×5), evaporated.

To the residue was added 6N HCl (1500 mL) and the mixture was refluxed overnight.

The mixture was extracted with EtOAc (2 L×5), concentrated, purified by silica gel column (petroleum ether:EtOAc=20:1) to give compound 3 as a yellow solid (80 g, 41% yield).

b. Preparation of Compound 4

To a mixture of compound 3 (150 g, 824 mol) in MeOH (2 L) at −10° C. was added NaBH$_4$ (31.2 g, 824 mmol) in portions. The mixture was stirred between −10° C. to 0° C. for 20 minutes, diluted with EtOAc (5 L), washed with sat. NH$_4$Cl aqueous solution, brine, dried over Na$_2$SO$_4$, concentrated. The residue was purified by silica gel column (petroleum ether:EtOAc=5:1) to give compound 4 as a yellow oil (90 g, 60% yield).

c. Preparation of Compound 5

To a solution of POCl$_3$ (2 ml, 21.6 mmol) in DCM (20 ml) was added compound 4 (2 g, 10.8 mmol), then TEA (3.6 ml, 27 mmol) in DCM (10 ml) was added at −40° C. under N$_2$, stirred at −40° C. for 5 hrs. Then 2-Bromoethylamine hydrobromide (17.6 g, 86.8 mmol) was added, TEA (12 ml, 86.8 mmol) in DCM (40 ml) was added slowly into above solution at −40° C., stirred for 0.5 h. K$_2$CO$_3$ (10%, 10.4 g, 100 ml) was added, stirred at r.t. for 5 mins. Extracted with DCM (300 ml×3), evaporated, purified by silica gel column (EtOAc) to give compound 5 as a yellow oil (2.3 g, 43% yield).

d. Preparation of Compound 6

A mixture of compound 5 (4 g, 8.42 mmol) and Ag$_2$O (5.85 g, 25.26 mmol) in THF (40 ml) was stirred at 65° C. for 3 hrs, filtered and concentrated. The residue was purified by silica gel column (EtOAc) to give compound 6 as a yellow oil (2.3 g, 87% yield).

e. Preparation of Compound TH2870

To a solution of Compound 7 (1.81 g, 10.95 mmol) in DMF (10 ml), NaH (60%, 438 mg, 1095 mmol) was added at 0° C., stirred for 10 mins, then compound 6 (2.3 g, 7.3 mmol) in DMF (10 ml) was added, stirred at 0° C. for 30 mins.

Quenched with H$_2$O, extracted with EtOAc (100 ml×5), washed with H$_2$O (150 ml), brine, evaporated, purified by silica gel column (DCM:MeOH=40:1) to give compound TH2870 as a yellow oil (2.3 g, 69% yield).

Figure 1B:
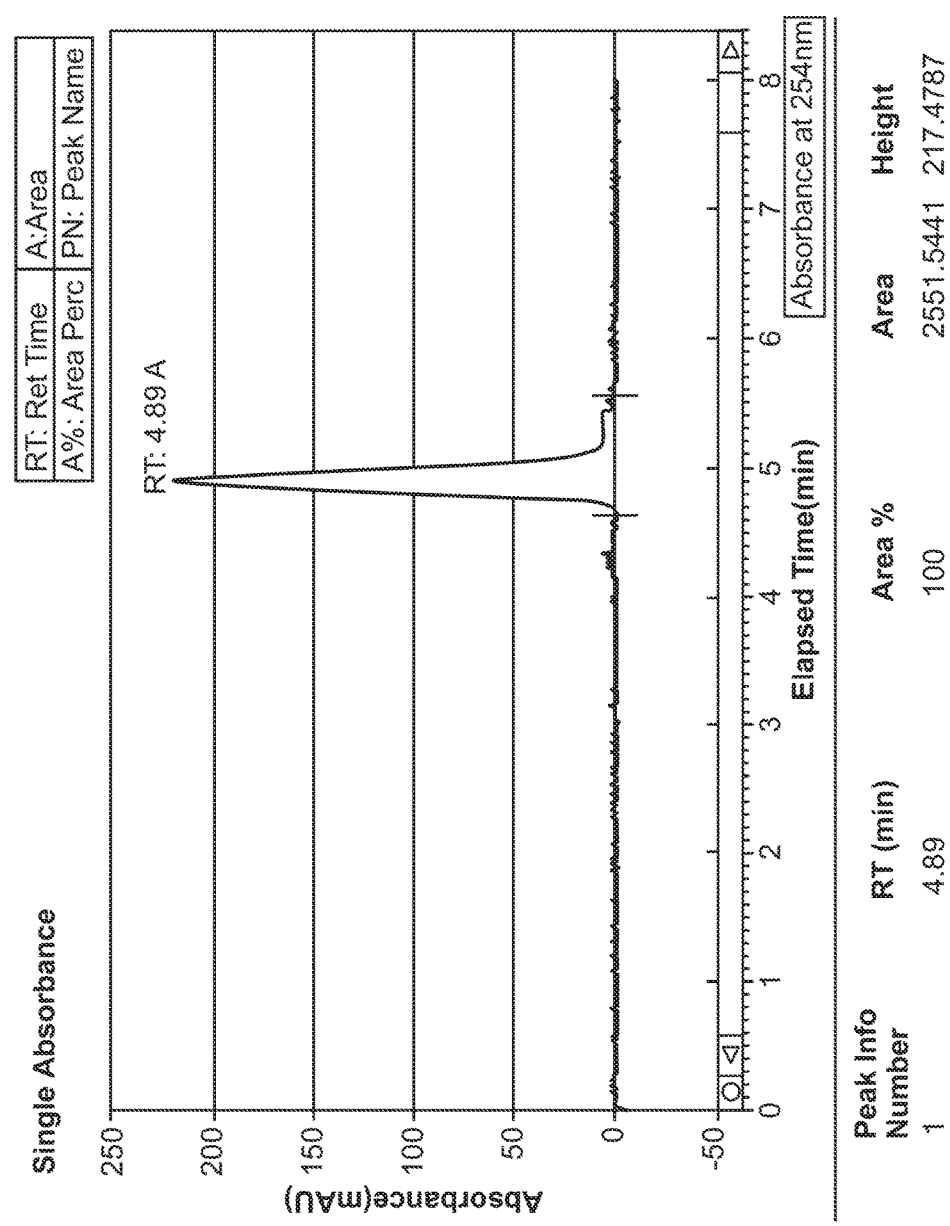
Figure 1C:
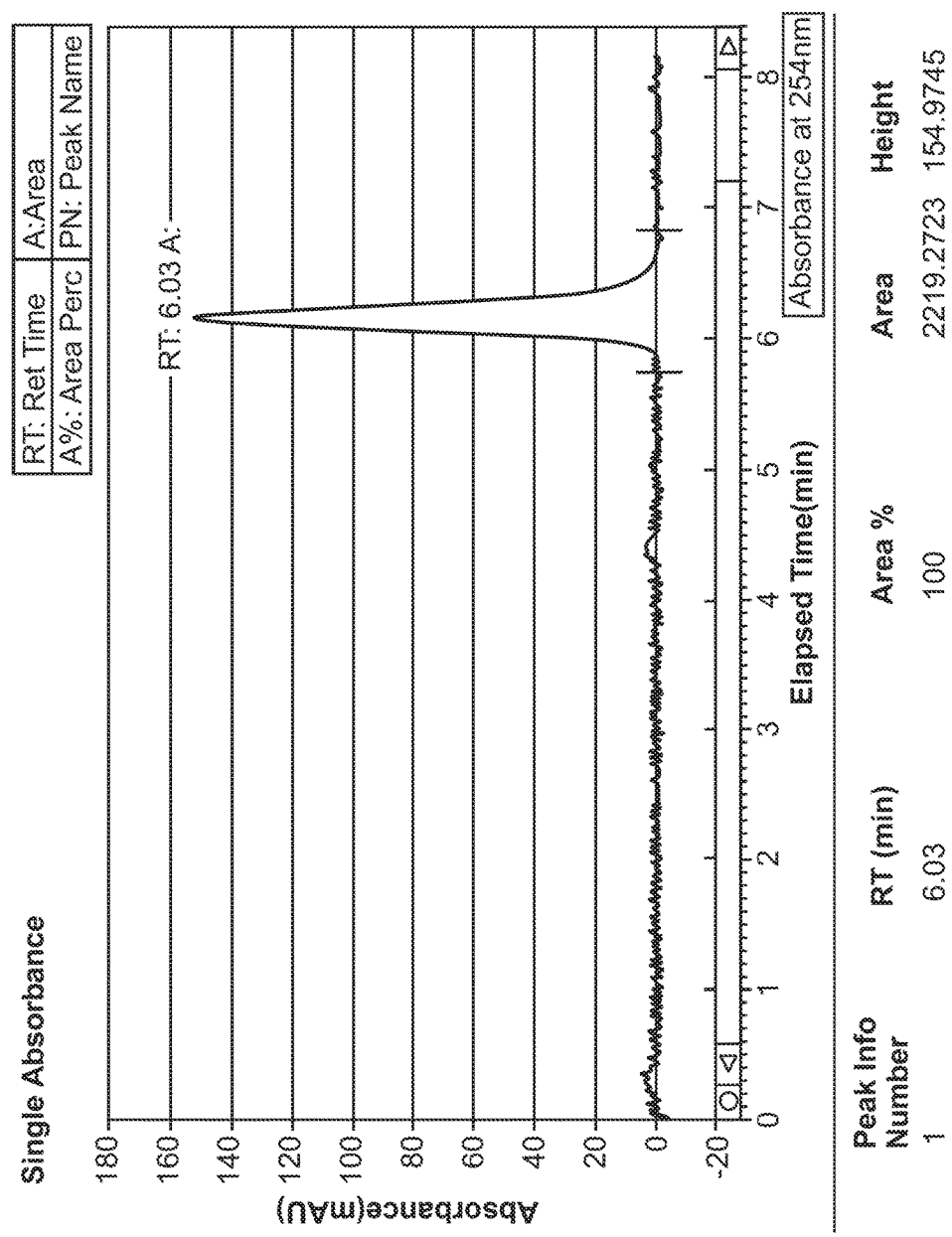

Example 3. Separation of the Enantiomers of TH2870 by Preparative Chiral Chromatography Dissolve 983 mg of compound of formula (I) in 36 mL of methanol, inject 1 mL onto a CHIRALPAK OZ-H 4.6×250 mm, 5 μm (Daicel) in a SFC-80 Method Station (Thar, Waters), at a flow rate of 3.0 ml/min and back pressure of 120 Bar at a column temperature of 35-40° C. and elute at that flow rate in a mixture of CO$_2$/Methanol (65-60/35-40). The enantiomer of formula (Ia) (configuration (R)) is obtained in a yield of 86.5% and with an enantiomeric purity of 100%. The enantiomer of formula (Ib) (configuration (S)) is obtained in a yield of 83.8% and with an enantiomeric purity of 100%. FIG. 1 shows a purity check of TH 2870 enantiomer 1 (TH 3423) and TH 2870 enatiomer 2 (TH 3424 or AST 106) after chiral separation by LCMS.

Chiral Synthesis of 7TH 3423 and 3424
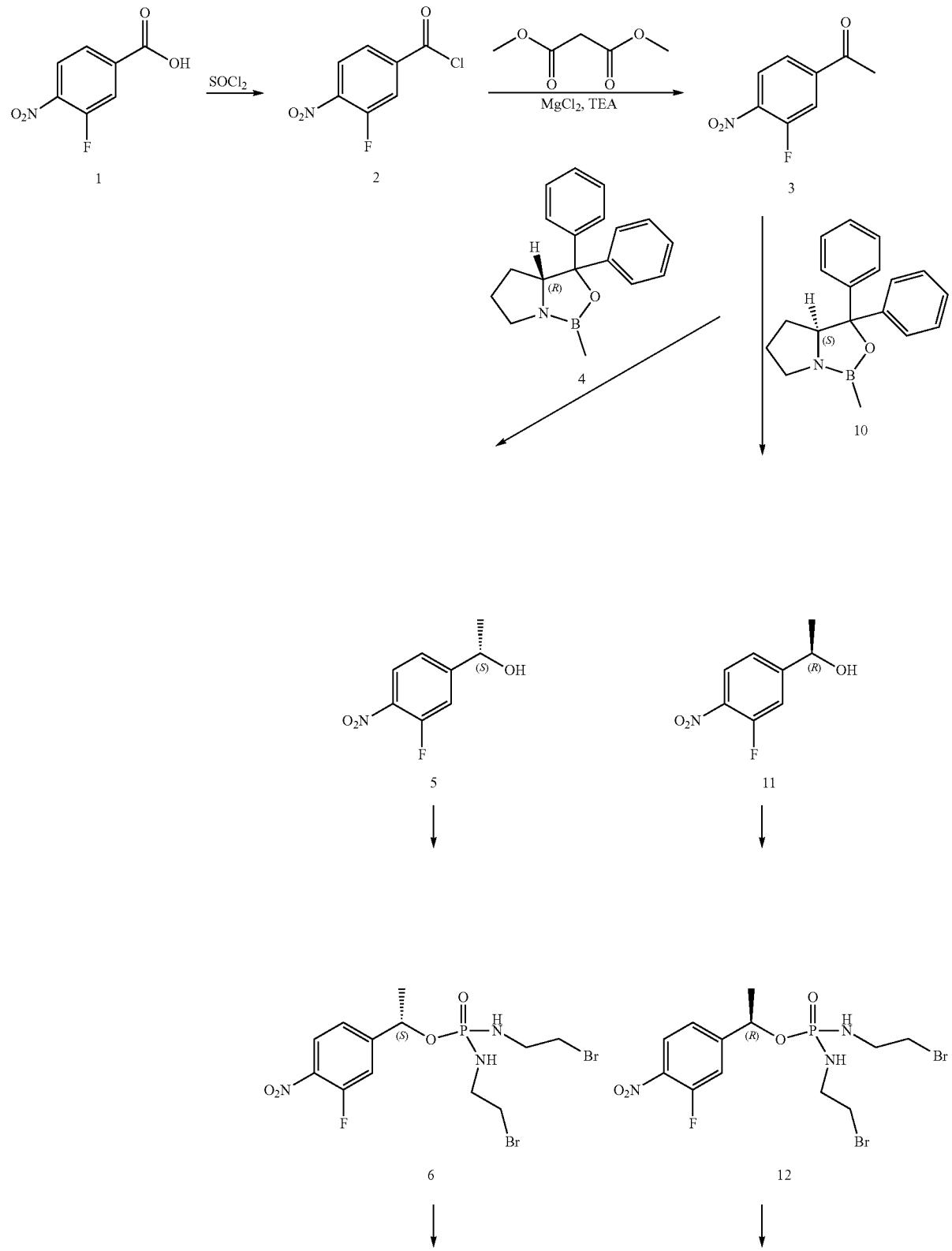

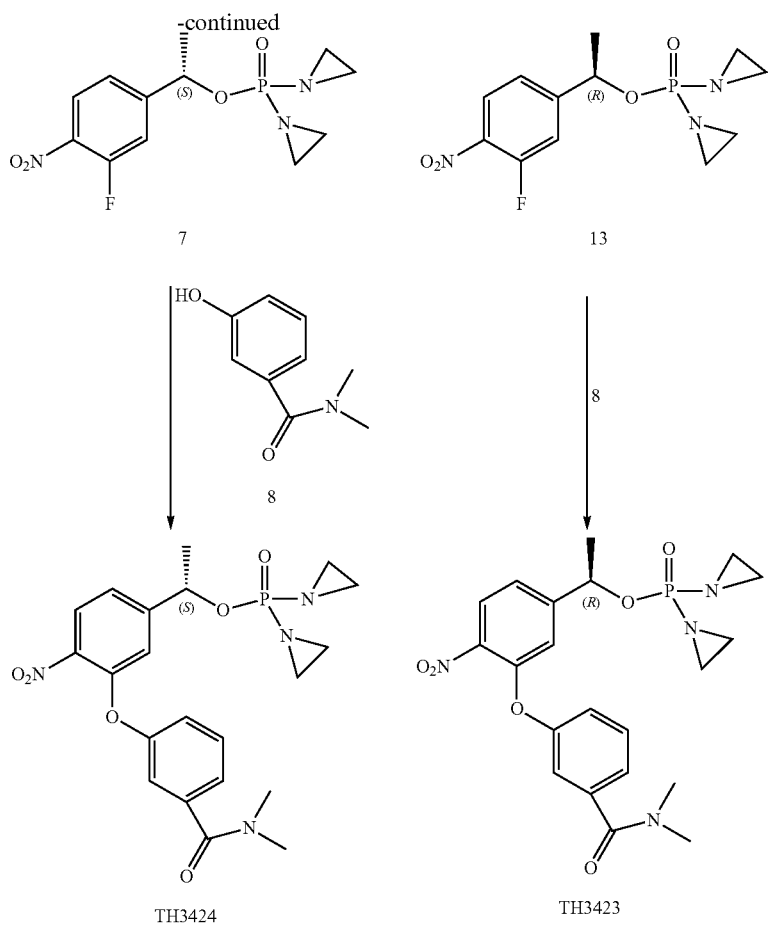

Compound 2

Compound 1 (65 g) was refluxed in SOCl$_2$ (150 mL) with DMF (2.5 mL) for 5 h to get a clear solution and then SOCl$_2$ was removed under vacuum. The residue was diluted with toluene (30 mL) and the solvents were removed again. The residue was used in the following step without further purification.

Compound 3

A mixture of MgCl$_2$ (21.0 g, 221 mmol), TEA (100.0 mL, 717 mmol) and dimethyl malonate (41.0 mL, 359 mmol) was stirred with mechanical stir at RT for 2 hrs before compound 2 in THF (80 ml) was added. The resulting mixture was stirred at RT for 4 hrs before conc. HCl (90 mL) was added and stirred for 30 minutes. The mixture was extracted with EtOAc (300 mL×3), concentrated under reduced pressure. To the residue was added 6N HCl (300 mL) and the mixture was refluxed overnight. The mixture was extracted with EtOAc (300 mL×3), organic layer was washed with NaHCO$_3$(aq.) and dried (Na$_2$SO$_4$), filtered and concentrated under reduced pressure. The residue was recrystallized from AcOEt/Hex=1/3(V/V) to afford compound 3 as a light yellow solid (46 g). $^1$H NMR (CDCl$_3$, 400 MHz) δ: 8.16 (d, 1H), 7.86 (t, 2H), 2.68 (s, 3H)

Compound 5:

Under argon, BH$_3$.THF (1M, 11 mL) was added to a solution of compound 4 in 1M toluene (3 mL, 3 mmol) at 0° C. The solution was stirred for 30 min. then cooled down to −40° C. A solution of compound 3 (1.83 g, 10 mmol) in THF (40 mL) was added slowly during 4 hrs at −40° C. The system was stirred at −40° C. for 2 hrs (TLC showed SM disappeared). MeOH (20 ml) was added to about solution at −40° C. and the solution was stirred for 30 min. After the solvents were removed at rt and the residue was purification by column (Hex/AcOEt=3/1 (V/V)) to get compound 5 (1.6 g).

$^1$HNMR (CDCl$_3$, 400 MHz) δ: 8.05 (t, 1H), 7.34 (d, 1H), 7.27 (d, 1H), 4.99 (m, 1H), 1.51 (d, 3H).

Compound 6

To a solution of POCl$_3$ (1.6 mL, 17.25 mmol) in DCM (10 mL) at −40° C. under argon was added compound 5 (1.6 g, 8.65 mmol), then TEA (2.9 mL, 22.9 mmol) in 10 mL DCM. The mixture was stirred at −40° C. for 6 hrs and then 2-Bromoethylamine hydrobromide (14.2 g, 69.3 mmol) was added, TEA (9.6 mL) in DCM (10 mL) was added dropwise. The reaction mixture was stirred from −40° C. to rt overnight. K$_2$CO$_3$ (8.3 g in 80 mL water) was added and mixture was stirred for 5 min. The mixture was extracted with DCM, dried over Na$_2$SO$_4$. Filtered, concentrated and then flash chromatography of silica gel, eluted with Acetone/Hexane=0-100%) to afford compound 6 as yellow oil (2.68 g, yield: 65%).

$^1$H NMR (CDCl$_3$, 400 MHz) δ: 8.08 (t, 1H), 7.32 (d, 1H), 7.29 (d, 1H), 5.56 (m, 1H), 3.34-3.56 (m, 2H), 3.32-3.42 (m, 4H), 3.08-3.26 (m, 4H), 1.62 (d, 3H). 31PNMR: 14.44.

Alternatively TH3424 can be Synthesized by the Following Procedure:

Toluene (11 ml/g) was added to a four necked glass bottle under nitrogen. Agitation as started, POCl3 was added (1.025 eq) to vessel 1 under nitrogen. The contents of vessel 1 was cooled to −2~2° C. The solution of compound 1 was added (1.0 eq) and TEA (1.435 eq) in toluene (11 ml/g) dropwise at −2~2° C. The contents of vessel 1 was agitated at −2~2° C. for at 1~2 hours. The contents was sampled for HPLC analyses for information. 2-Bromoethylaminehydrobromide (3 eq) was added to vessel 1. TEA (6 eq) was added to vessel 1 dropwise at −2~2° C. The contents of vessel 1 was agitated at 0° C.~RT overnight. The contents was sampled for HPLC analyses. Workup procedure was as follows: H2O (19 ml/g) was added to vessel 1 and stir for 5~10 min. The mixture was extracted with EA (19 ml/g) for three times. The organic phase was dried over Na2SO4 and filtered. The mother liquor was concentrated at 40~50° C. The crude product was purified by chromatography of silica gel to get the purified product.

Alternatively TH3424 can be Synthesized by the Following Procedure:

Toluene (11 ml/g) was added to a four necked glass bottle under nitrogen. Agitation was started and compound 1 (1.0 eq) and TEA (1.435 eq) were added to vessel 1 under nitrogen. The contents of vessel 1 were cooled to −2~2° C. POCl3 (1.025 eq) was added to vessel 1 under nitrogen dropwise at −2~2° C. The contents of vessel 1 were agitated at −2~2° C. for at 1~2 hours. The contents were sampled for HPLC analyses for information. 2-Bromoethylamine hydrobromide (3 eq) was added to vessel 1. TEA (6 eq) was added to vessel 1 dropwise at −2~2° C. The contents of vessel 1 were agitated at 0° C.~RT overnight. The contents were sampled for HPLC analyses. The workup procedure was the same as above.

Alternatively TH3424 can be Synthesized by the Following Procedure:

DCM (2.2 ml/g) and POCl3 (1.91 eq) were added to a four necked glass bottle under nitrogen. The agitation was started and the contents of vessel 1 were cooled to −35~−40° C. under nitrogen. Compound 1 (1.0 eq)/DCM (4.5 g/ml) solution was added to vessel 1 under nitrogen dropwise at −35~−40° C. TEA (4.0 eq)/DCM (4.5 g/ml) solution was added to vessel 1 under nitrogen dropwise at −35~−40° C. The contents of vessel were agitated 1 at −35~−40° C. for at 4~6 hours. The contents were sampled for HPLC analyses for information. 2-Bromoethylamine hydrobromide (8 eq) was added to vessel 1 at −30~−40° C. TEA (12 eq) was added to vessel1 dropwise at −30~−40° C. The contents of vessel 1 were agitated at −30~−40° C. for 1-2 h. The contents were sampled for HPLC analyses. Workup procedure: H2O (15 ml/g) was added to vessel 1 and stirred for 5~10 min. The aqueous phase was extracted with DCM (12.5 ml/g) for one time. The organic phase was dried over Na2SO4 and filtered. The filtrate was concentrated at 20~30° C. The crude product was purified by chromatography to get the purified product.

Compound 7

A mixture of compound 6 (2.68 g), Ag$_2$O (3.92 g), in THF (30 mL) was stirred at 55° C. overnight. After removal of solvent under vacuum, the residue was separated by flash chromatography on silica gel to yield light liquid 1.0 g of compound 7.

$^1$H NMR (CDCl$_3$, 400 MHz) δ: 8.05 (t, 1H), 7.34 (d, 1H), 7.29 (d, 1H), 5.66 (m, 1H), 2.02-2.24 (m, 8H), 1.61 (d, 3H). 31PNMR: 31.55.

TH 3424 (TH 2870 Enantiomer 2)

A mixture of compound 7 (1.0 g), compound 8 (785 mg), K$_2$CO$_3$ (880 mg) in DMF (8 mL) was stirred at rt overnight. The mixture was diluted with water, extracted with DCM, dried over Na$_2$SO$_4$. Filtered, concentrated and then flash chromatography to afford compound 9 as yellow oil (1.1 g).

$^1$H NMR (CDCl$_3$, 400 MHz) δ: 7.97 (d, 1H), 7.41 (t, 1H), 718-7.27 (m, 4H), 7.02-7.12 (m, 3H), 5.59 (m, 1H), 3.08 (s, 3H), 2.97 (s, 3H), 2.01-2.21 (m, 8H), 1.66 (d, 3H). 31P NMR: 31.27.

Compound 11

Same procedure with compound 5. Compound 8 was used instead of compound 3. Yield: 50%

$^1$H NMR (CDCl$_3$, 400 MHz) δ: 8.05 (t, 1H), 7.34 (dd, 1H), 7.27 (d, 1H), 4.99 (m, 1H), 1.51 (d, 3H).

Compound 12

Same procedure with compound 6 (yield: 35%).

$^1$H NMR (CDCl$_3$, 400 MHz) δ: 8.08 (t, 1H), 7.32 (d, 1H), 7.29 (d, 1H), 5.56 (m, 1H), 3.34-3.56 (m, 2H), 3.32-3.42 (m, 4H), 3.08-3.26 (m, 4H), 1.62 (d, 3H). $^{31}$PNMR: 14.47.

Compound 13

Same procedure with compound 7 (yield: 36%). $^1$H NMR (CDCl$_3$, 400 MHz) δ: 8.06 (t, 1H), 7.34 (d, 1H), 7.30 (d, 1H), 5.67 (m, 1H), 2.02-2.25 (m, 8H), 1.62 (d, 3H). $^{31}$PNMR: 31.56.

TH3423 (7TH 2870 Enatiomer 1)

Same procedure with compound 9 (yield: 68%). $^1$H NMR (CDCl$_3$, 400 MHz) δ: 7.97 (d, 1H), 7.41 (t, 1H), 718-7.27 (m, 4H), 7.02-7.12 (m, 3H), 5.59 (m, 1H), 3.08 (s, 3H), 2.97 (s, 3H), 2.01-2.21 (m, 8H), 1.66 (d, 3H). $^{31}$P NMR: 31.25.

Example 4. In Vitro Human Tumor Cell Line Cytotoxicity Assay

In vitro proliferation data on the H460 non cell lung cancer human tumor cell line is reported above in the compound table. IC$_{50}$ values are reported in micromolar and result from exposure of compound at various concentrations for 2 hrs followed by a wash step and addition of fresh media followed by growth and cell viability staining and comparison to a media only treated control.

Specifically, exponentially growing cells were seeded at a density of 4×10$^3$ cells per well in a 96 well plate and incubated at 37° C. in 5% CO$_2$, 95% air and 100% relative humidity for 24 hours prior to addition of test compounds. Compounds were solubilized in 100% DMSO at 200 times the desired final test concentration. At the time of drug addition, compounds were further diluted to 4 times the desired final concentration with complete medium. Aliquots of 50 μl of compound at specified concentrations were added to microtiter wells already containing 150 μl of medium, resulting in the final drug concentration reported. After drug addition, the plates were incubated for an additional 2 hours at 37° C., 5% CO$_2$, 95% air, and 100% relative humidity, then the drug was washed off and fresh medium was added and the plates were incubated for addition 70 hrs at 37° C., 5% C02, 95% air and 100% relative humidity. At the end of this incubation, the viable cells were quantified using the AlamarBlue assay. The drug concentration resulting in growth inhibition of 50% (IC$_{50}$) was calculated using Prism software (Irvine, Calif.), and the results were listed in the table.

Its anti-proliferation efficacy on H460 lung cancer cells is also tabulated below.

| Compound number | Structure | IC 50 in proliferation assay in H460 cells (μM) |
|---|---|---|
| TH 2870 (racemate) | 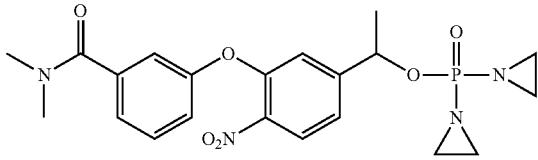 [SMILES: CC(OP(=O)(N1CC1)N1CC1)c1ccc([N+](=O)[O-])c(Oc2cccc(C(=O)N(C)C)c2)c1] | 0.005 |
| TH3423 | 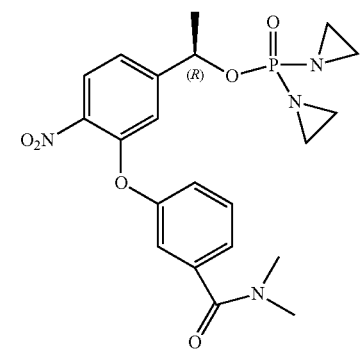 | 0.005 |
| TH3424 | 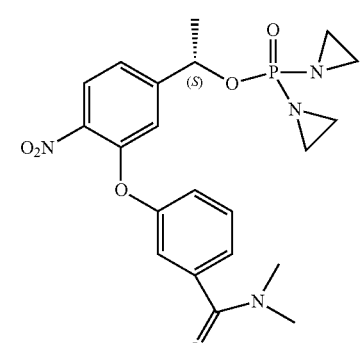 | 0.004 |

The H460 data above demonstrates a substantial anti-tumor effect with inhibition at down to low nanomolar levels for various compounds for only a 2 hr. exposure.

Example 5. Activation of TH 2870 by the Aldoketo Reductase, AKR1C3

Recombinant human AKR1C3 was diluted to 25 μg/mL in phosphate buffered saline (PBS), pH 7.4 (37° C.), containing 2 mM NADPH. TH2870 or progesterone (positive control) in 30% methanol/70% water was added to the reaction mixture at a final concentration of 5 μM and incubated at 37° C. for 120 minutes. At various times up to 120 min, 50 μL of the reaction mixture was taken and 200 μL acetonitrile containing propranolol as internal standard was added, vortex-mixed and centrifuged for 10 min. The resulting supernatant (5 μL) was injected into a LC/MS/MS for quantitation of % remaining TH 2870 and progesterone. The compounds were tested in duplicates.

Figure 2:
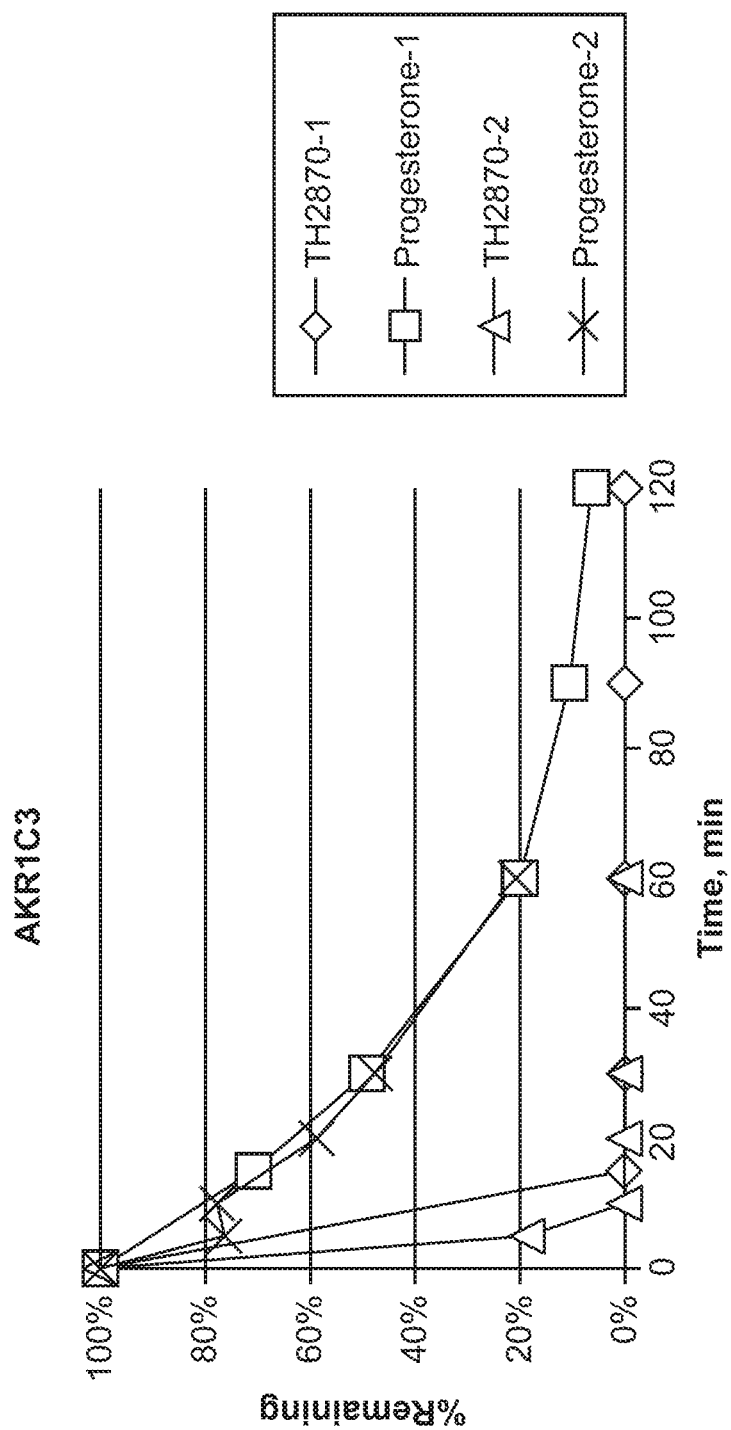
FIG. 2 illustrates the activation of TH 2870 by the aldoketo reductase, AKR1C3 compared to progesterone.

The data in FIG. 2 demonstrates the rapid disappearance of TH 2870 in the presence of AKR1C3 while the known substrate Progesterone is reduced slowly. Buffer controls containing NADPH but no enzyme showed no reaction in with either compound (data not shown).

Example 6. In Vitro Human Tumor Cell Line Cytotoxicity Assay

TH 2870, TH 3423 and TH 3424 was also tested in different cancer cell lines using the materials and procedures as follows. 10*cell lysate buffer (cell signaling technology, Cat. No. 9803); Protease Inhibitor Cocktail for Mammalian Tissues (Sigma, Cat. No. P8340); Phosphatase Inhibitor Cocktails for Serine/Threonine Phosphatases and L-Isozymes of Alkaline Phosphatases (Sigma, Cat. No. P0044); Phosphatase Inhibitor Cocktails for Tyrosine Protein Phosphatases, Acid and Alkaline Phosphatases (Sigma, Cat. No. P5726); BCA kit (Thermo, Cat. No. 23225); Primary antibody, mouse monoclonal AKR1C3 antibody (clone NP6.G6.A6; Sigma-Aldrich); Primary antibody, α-tubulin (clone B-5-1-2; Sigma-Aldrich); Secondary antibody, Goat-anti-Mouse IgG HRP conjugated (A4416; Sigma-Aldrich) were used. Cells were passaged two generations in good condition and digested. The appropriate number of cells were inoculated in 6-cm cell culture dishes, and incubated at 37° C., 5% CO2 overnight. When the cells were grown to 80% density, the dish was removed from incubator. The medium was aspirated, washed twice with ice-cold PBS, and residual PBS was removed. An appropriate volume of ice-cold 1*cell lysate was added and incubated on ice for 10 minutes. Cell lysate was transferred to microfuge tubes chilled in ice, 4° C., 12,000 rpm and centrifuged for 15 minutes. Supernatant was transferred into another microcentrifuge tube. Cell lysates were diluted by a 10*cell lysates, and add Protease Inhibitor Cocktail for Mammalian Tissues (Sigma, # P8340), Phosphatase Inhibitor Cocktails for Serine/Threonine Phosphatases and L-Isozymes of Alkaline Phosphatases, Phosphatase Inhibitor Cocktails for Tyrosine Protein Phosphatases, Acid and Alkaline Phosphatases. The BCA protein quantification kit for protein quantification was used with 1*cell lysate to dilute the cell lysate to the same concentration. Corresponding samples were added on 5*SDS-loading buffer, heated to 85° C. for 10 minutes, and centrifuged briefly. The samples were saved at −20° C. or used directly for protein electrophoresis. The samples were saved at −20° C. or used directly for protein electrophoresis. Those samples were electrophoresed according to standard practice, transferred to a membrane, the primary antibodies and then secondary antibody were applied according to the manufacturer's instructions. Odyssey infrared laser imaging system was used to scan signals.

Figure 3:
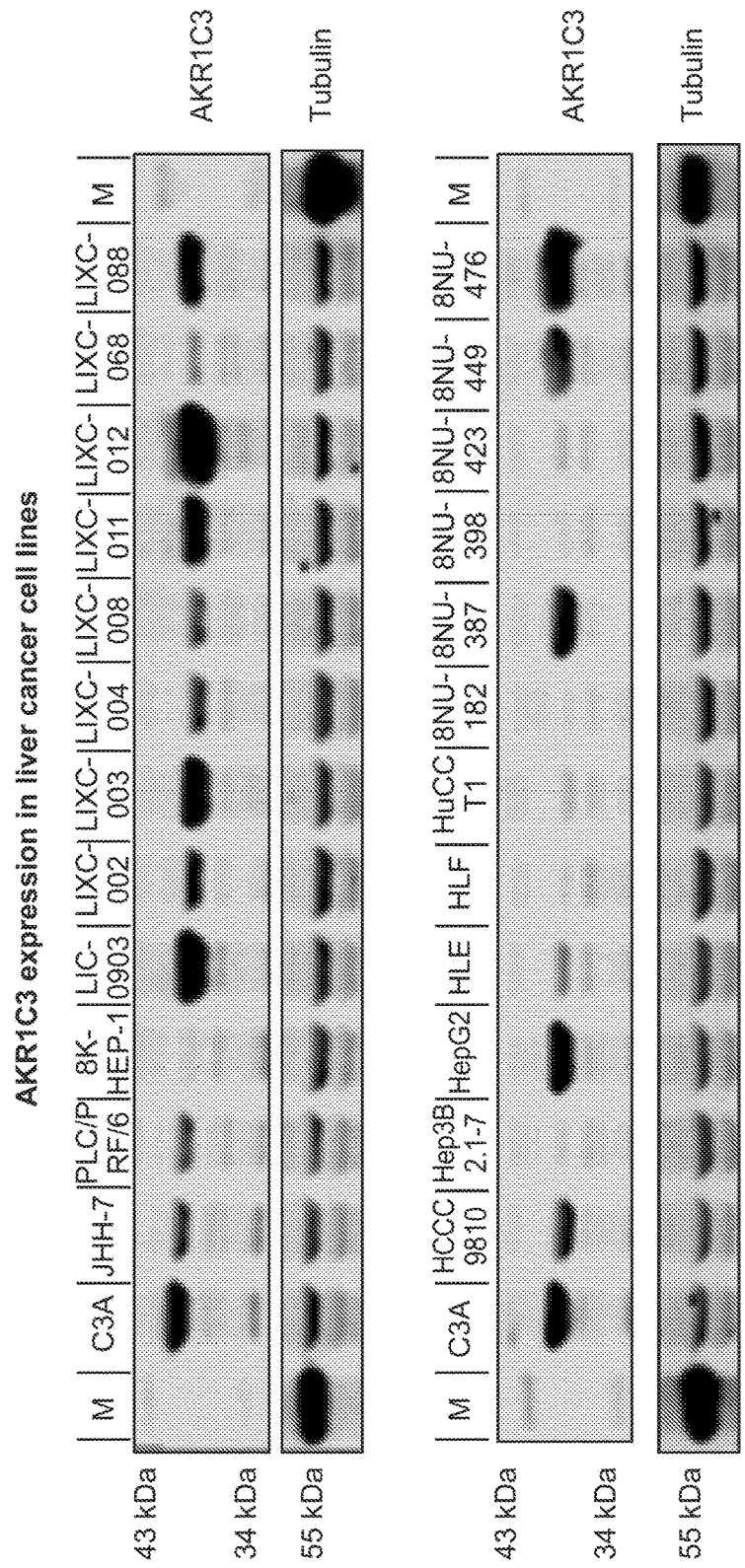
FIG. 3 illustrates AKR1C3 expression in liver cancer cell lines.
Figure 4:
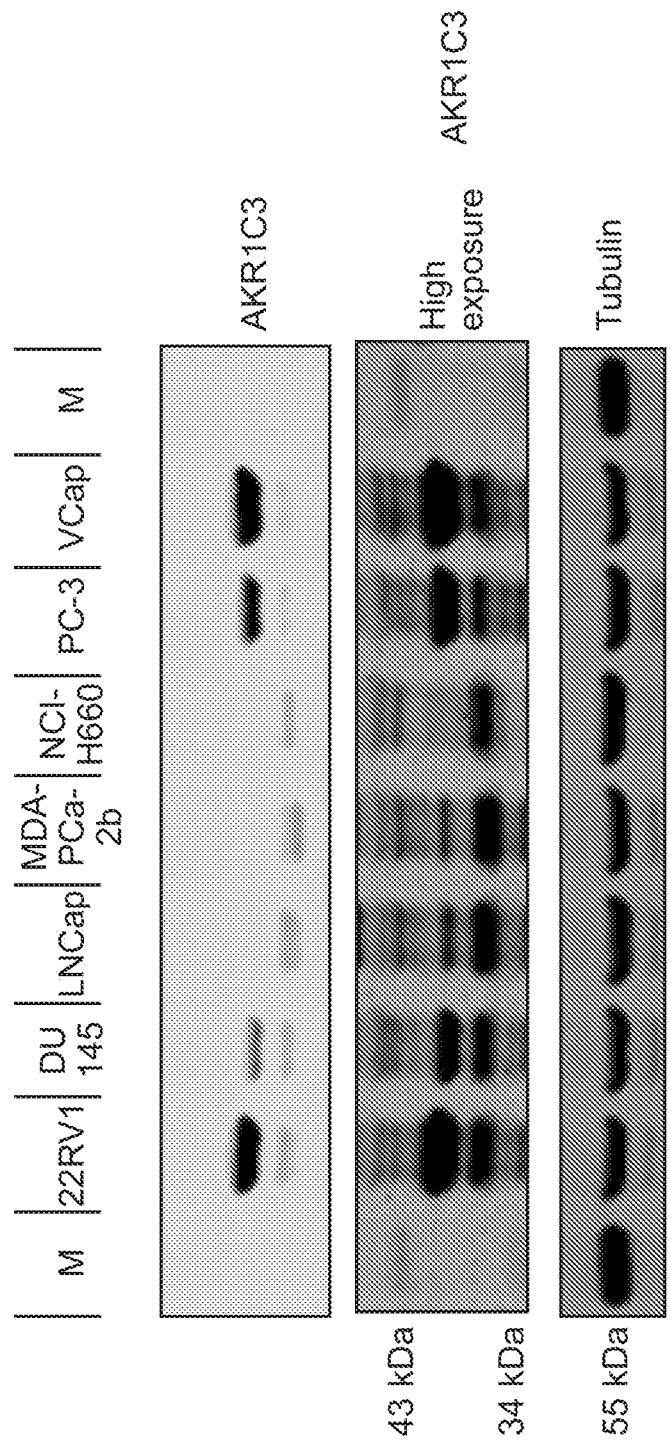
FIG. 4 illustrates AKR1C3 expression in prostate cancer cell lines.

The results are shown below in FIGS. 3 and 4 and listed in the following tables:

TABLE

TH 2870, TH 3423 and TH 3424 sensitivity in liver, prostate, esophageal cancer and leukemia cell lines

| Liver cancer cell line | Compound ID | Min Inhibition % | Max Inhibition % | RelIC50 (μM) | AbsIC50 (μM) |
|---|---|---|---|---|---|
| HepG2 | TH3424 | 3.4 | 100.2 | 0.0073 | 0.0086 |
| HepG2 | TH3423 | −7.2 | 99.5 | 0.0131 | 0.0187 |
| HepG2 | TH2870 | 3.3 | 98.9 | 0.0055 | 0.0064 |
| C3A | TH3424 | −2.1 | 98.7 | 0.0041 | 0.0093 |
| C3A | TH3423 | 5.4 | 98.5 | 0.0096 | 0.0117 |
| C3A | TH2870 | 8.1 | 98.1 | 0.0071 | 0.0062 |
| HCCC9810 | TH3424 | 2.1 | 95.4 | 0.0134 | 0.0139 |
| HCCC9810 | TH3423 | 0.0 | 93.7 | 0.0168 | 0.0187 |
| HCCC9810 | TH2870 | −2.6 | 95.4 | 0.0292 | 0.0294 |
| PLCPRF5 | TH3424 | 1.4 | 85.2 | 0.1279 | 0.1107 |
| PLCPRF5 | TH3423 | −4.9 | 77.7 | 0.1556 | 0.2066 |
| PLCPRF5 | TH2870 | −1.7 | 53.3 | 0.4745 | 0.5750 |
| SNU-387 | TH3424 | −14.8 | 99.3 | 0.0587 | 0.0701 |
| SNU-387 | TH3423 | 1.3 | 99.8 | 0.0463 | 0.0397 |
| SNU-387 | TH2870 | 1.7 | 102.8 | 0.0422 | 0.0340 |
| LIXC012 | TH3424 | 4.1 | 82.8 | 0.0112 | 0.0175 |
| LIXC012 | TH3423 | −1.1 | 84.8 | 0.0081 | 0.0169 |
| LIXC-012 | TH2870 | 6.6 | 87.1 | 0.0274 | 0.0187 |
| Vcap_TH3424 | Vcap_TH3424 | −13.2 | 101.4 | 0.0132 | 0.0148 |
| Vcap | TH3423 | 1.1 | 101.0 | 0.0266 | 0.0216 |
| Vcap | TH2870 | −3.4 | 100.2 | 0.0227 | 0.0152 |
| TE-11 | TH3424 | | | 0.0027 | |
| TE-14 | TH3424 | | | 0.0047 | |
| OE 21 | TH3424 | | | 0.0052 | |
| T.T | TH3424 | | | 0.006 | |
| TE-6 | TH3424 | | | 0.021 | |
| TE-9 | TH3424 | | | 0.011 | |
| ECa-109 | TH3424 | | | 0.017 | |
| KYSE | TH3424 | | | 0.011 | |
| TE-4 | TH3424 | | | 0.0099 | |
| TE-8 | TH3424 | | | 0.019 | |
| TE-15 | TH3424 | | | 0.0029 | |
| COLO680N | TH3424 | | | 0.066 | |
| EC-GI-10 | TH3424 | | | 0.013 | |
| KYSE 70 | TH3424 | | | 0.033 | |
| TE-5 | TH3424 | | | 0.033 | |
| OE 33 | TH3424 | | | 0.084 | |
| KYSE 510 | TH3424 | | | 0.18 | |
| KYSE 270 | TH3424 | | | 0.27 | |
| KYSE 180 | TH3424 | | | 0.45 | |
| CCRF-CEM | TH3424 | | | 0.0037 | |
| MOLT-4 | TH3424 | | | 0.010 | |
| PF-382 | TH3424 | | | 0.015 | |
| SUP-T1 | TH3424 | | | 0.003 | |
| TALL-1 | TH3424 | | | 0.03 | |
| Jurkat | TH3424 | | | 0.04 | |
| Jurkat, Clone E6-1 | TH3424 | | | 0.024 | |
| NOMO-1 | TH3424 | | | 0.011 | |
| P116 | TH3424 | | | 0.084 | |
| P30/OHK | TH3424 | | | >1 | |
| GR-ST | TH3424 | | | 0.099 | |
| KG-1 | TH3424 | | | 0.0153 | |
| TF-1 | TH3424 | | | 0.028 | |
| HEL | TH3424 | | | 0.224 | |
| Reh 3 | TH3424 | | | 0.003 | |
| HL-60 | TH3424 | | | 0.003 | |
| HL-60 Clone | TH3424 | | | 0.0526 | |
| K-562 | TH3424 | | | >1.0 | |
| ATN-1 | TH3424 | | | 0.0298 | |
| Mono-Mac-6_ | TH3424 | | | >1.0 | |
| THP-1_ | TH3424 | | | >1.0 | |

Example 7. In Vivo Human Tumor Xenograft Models and Antitumor Activity

Three human xenograft anti-tumor models utilizing non-small cell lung H460, non-small cell lung A549, and melanoma A375 models were used to demonstrate the efficacy of the compounds provided herein.

Specific pathogen-free homozygous female nude mice (nu/nu, Charles River Laboratories) were used. Mice were given food and water ad libitum and housed in microisolator cages. Four to six week old animals were identified by microchips (Locus Technology, Manchester, Md., USA) at the time of the experiments. All animal studies were approved by the Institutional Animal Care and Use Committee at Threshold Pharmaceuticals, Inc.

All cell lines were from the American Type Culture Collection (ATCC, Rockville, Md., USA). Cells were cultured in the suggested medium with 10% fetal bovine serum and maintained in a 5% $CO_2$ humidified environment at 37° C.

Cells were mixed with Matrigel (30% in H460) and 0.2 ml per mouse were subcutaneously implanted to the flank area of the animals. When tumor size reached 100-150 $mm^3$, mice were randomized into experimental or vehicle groups with 10 mice/group and treatment was started (Day 1). The tested compounds were formulated in 5% DMSO in D5W. All compounds were given by IP, QD×5/wk (5 days on, 2 days off) as one cycle, for a total of 2 cycles. Tumor growth and body weight were measured twice a week. Tumor volume was calculated as (length×$width^2$)/2. Drug efficacy was assessed as Tumor Growth Inhibition (TGI) and Tumor Growth Delay (TGD). TGI was defined as (1−ΔT/ΔC)×100, where ΔT/ΔC presented the ratio of the change in mean (or median, if variation within the group was relatively large) tumor volume of the treated group and of the control group. TGD was calculated as the extra days for the treated tumor to reach 500 $mm^3$ as compared to the control group. Animals were culled when individual tumor size reached over 2000 $mm^3$ or mean tumor volume exceeded 1000 $mm^3$ in the group. Data are expressed as the mean±SEM. One-way analysis of variance with Dunnett post comparison test (GraphPad Prism 4) or two-tailed student's t-test were used for analysis. A P level <0.05 was considered statistically significant.

Example 8. In Vivo Efficacy Results

This study employed an A375 melanoma human tumor xenograft model and the compounds provided herein were compared to thiotepa and the approved anti melanoma drug, Abraxane. The antitumor effects and the safety of administration are graphically illustrated below. Mpk refers to mg/kg.

| Group | Days to 500 mm³ | Days to 1000 mm³ | TGD500, Days (vs. vehicle) | TGD1000, Days (vs. vehicle) | TGI |
|---|---|---|---|---|---|
| Group 1: Vehicle, qdx5x2, ip | 15 | 25 | | | |
| Group 2: Thio-TEPA, 2.5 mpk, qdx5x2, ip | 18 | 27 | 3 | 2 | 16.6% |
| Group 4: Abraxane, 30 mpk, 2x/wkx2, iv | 24 | 35 | 9 | 10 | 47.4% |
| Group 8: TH2870, 20 mpk, qdx5x2, ip | | | | >13 | 98.0% |

Taken together these studies demonstrate significant antitumor efficacy in 3 different tumor cell lines relative to standard chemotherapeutics.

Example 9. TH3424 in Mouse Model of Human Liver Cancer

Female athymic nude mice (6 weeks of age) were used in this study. The animals were purchased from Beijing HFK Bioscience, Co., Ltd and maintained in a High Efficiency Particulate Air Filter (HEPA) filtered environment with cages, food, and bedding sterilized by irradiation or autoclaving. A total of 32 nude mice were used for the study. HepG2-GFP human hepatocellular carcinoma cells (Anti-Cancer, Inc., San Diego, Calif.) were incubated with RPMI-1640 (Gibco-BRL, Life Technologies, Inc.), which contained 10% FBS. Cells were grown in a $CO_2$ Water Jacketed Incubator (Forma Scientific) maintaining 37° C. and a 5% $CO_2$/95% air atmosphere. Cell viability was determined by trypan blue exclusion analysis. Five female athymic nude mice were injected subcutaneously with a single dose of $5\times10^6$ HepG2-GFP cells. Tumors were harvested when their size reached 1 cm³ and the tumor tissues were then cut into small fragments of 1 mm³. Forty female nude mice were implanted orthotopically with a single piece of tumor fragment, which was derived from a subcutaneous tumor model of HepG2-GFP human hepatocellular carcinoma. The tumor tissue was orthotopically implanted in the right lobe of the liver in each mouse by SOI (Surgical Orthotopic Implantation). Briefly, an upper abdominal incision of 1 cm was made under anesthesia. Right lobe of the liver was exposed and a part of the liver surface was injured mechanically by scissors. Then a piece of tumor fragment was fixed within the liver tissue, the liver was returned to the peritoneal cavity and the abdominal wall finally closed. Mice were kept in laminar-flow cabinets under specific pathogen-free-conditions.

Treatment was started three days after tumor implantation when the implanted tumors reached an average size of around 1 mm². The 32 tumor-bearing mice were randomly divided into four experimental groups of 8 mice each. Each cage was clearly marked for its group with four mice per cage. Each mouse had an earmark for identification. The table below shows the study design.

TABLE

| Groups and treatment protocol | | | | | |
|---|---|---|---|---|---|
| Groups (Agent) | Dose | Volume | Dosing schedule | Route | Animal (n) |
| Saline (C) | 0.9% | 200 µl | Qdx35 | IP. | 8 |
| Sorafenib (S) | 30 mg/kg | 100 µl | Qdx35 | Gavages | 8 |
| TH3424 | 2.5 mg/kg | 200 µl | QWx6 | IP. | 8 |
| TH3424 | 5 mg/kg | 200 µl | QWx3 | IP. | 8 |

Note: The treatment was initiated on day 3 post tumor implantation.

Figure 5:
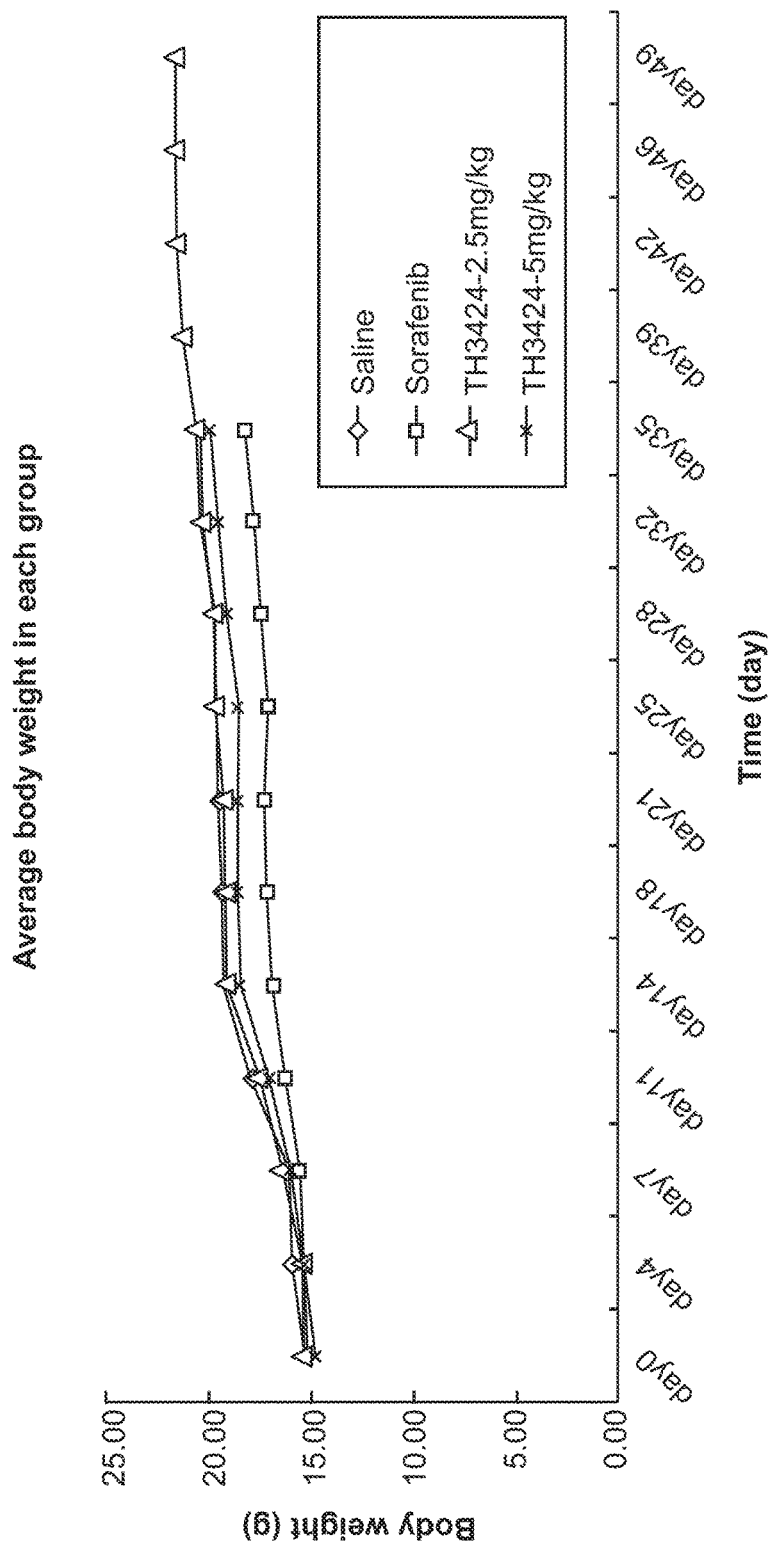
FIG. 5 illustrates average body weight in each group.

During the period of the study, all of the experimental mice were checked daily for mortality or signs of morbidity. The animals were observed till day 38 after tumor implantation. The body weights of the mice were measured twice weekly during the study period. Images of tumor growth and progression were acquired twice a week during the period of the study with the FluorVivo imaging system, Model 300/Mag (INDEC, CA, USA). All experimental animals were euthanized by injection of over-dose pentobarbital sodium on day 38 after tumor implantation. Livers were exposed for imaging, after which the tumors were removed and weighted with an electronic balance (Sartorius BS 124 S, Germany). Tumor tissues were kept in formalin for further analysis. Comparisons of body weights and tumor burdens in different groups were analyzed using the Student's t-test with an α=0.05 (two-sided). After intravenously injection of the test agents, the mice had no lying, no autonomous activity reduction. The experimental animals were generally in good condition. The body weight changes in each group are shown in FIG. 5 and the Table below.

TABLE

| Comparison of mean mice body weight at the end of the study | | | | |
|---|---|---|---|---|
| Groups | Day 0, Body Weight (g) (mean ± sd) | Day 35, Body Weight (g) (mean ± sd) | Body Weight Growth Rate (%) | P value |
| SALINE (C) | 15.2 ± 0.9 | 20.4 ± 0.9 | 34 | |
| SORAFENIB (S) | 15.1 ± 1.1 | 18.2 ± 0.8 | 21 | P = 0.0032 vs C |
| TH3424 (2.5 mg/kg) | 15.4 ± 0.6 | 21.7 ± 0.7 | 41 | P = 0.7252 vs C |

TABLE-continued

Comparison of mean mice body weight at the end of the study

| Groups | Day 0, Body Weight (g) (mean ± sd) | Day 35, Body Weight (g) (mean ± sd) | Body Weight Growth Rate (%) | P value |
|---|---|---|---|---|
| TH3424 (5 mg/kg) | 14.8 ± 1.2 | 19.9 ± 1.3 | 34 | P = 0.1740 vs C<br>P = 0.1869 vs (TH3424 2.5 mg/kg) |

As shown in FIG. 5 and the table above, on day 35 of the study, the average body weight of the mice in each group were increased by 21% to 41%. There was no statistically significant difference among TH2870-2 groups and negative control group. This suggested that there was no obvious acute toxicity to the experimental mice by intra-peritoneal administration of low or high dose of TH2870-2. In the sorafenib treated group, however, the average body weight was statistically significant lower than that in the negative control group. It suggested that there was a certain degree of toxicity to the experimental mice by administration of sorafenib at the tested dosage.

Tumor Progression in Each Group.

Figure 6:
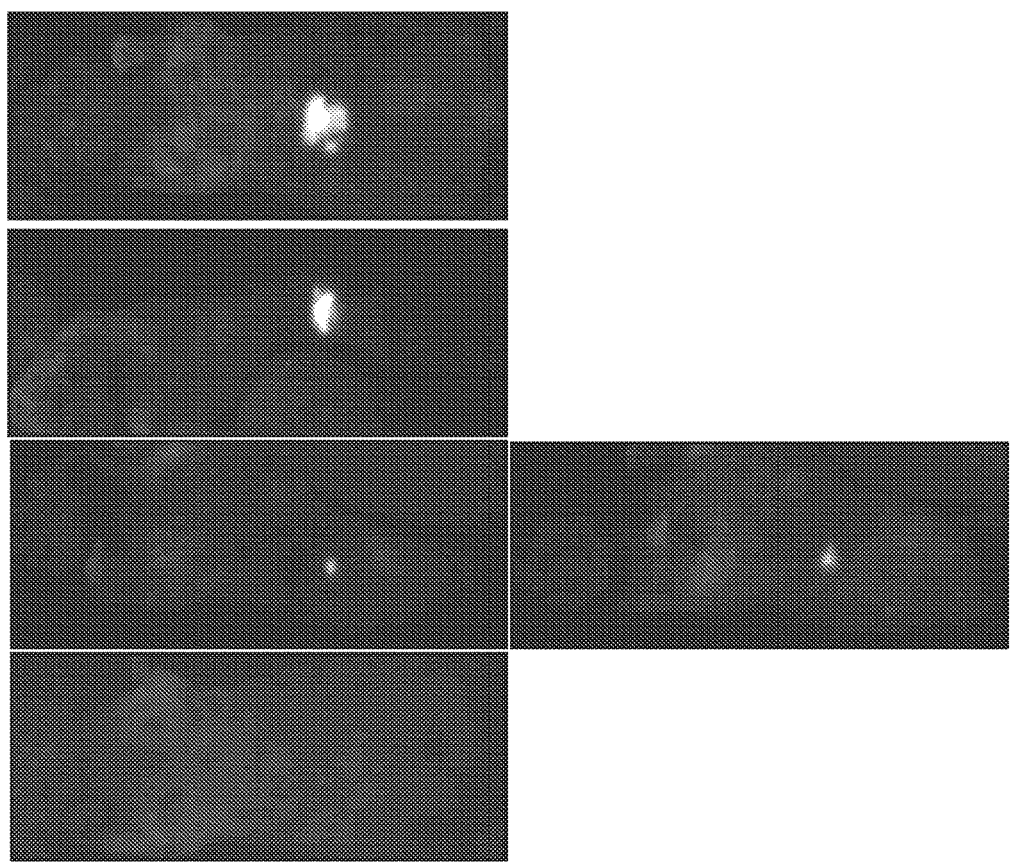
FIG. 6 illustrates typical fluorescence images of tumor burden in each group.
Figure 7:
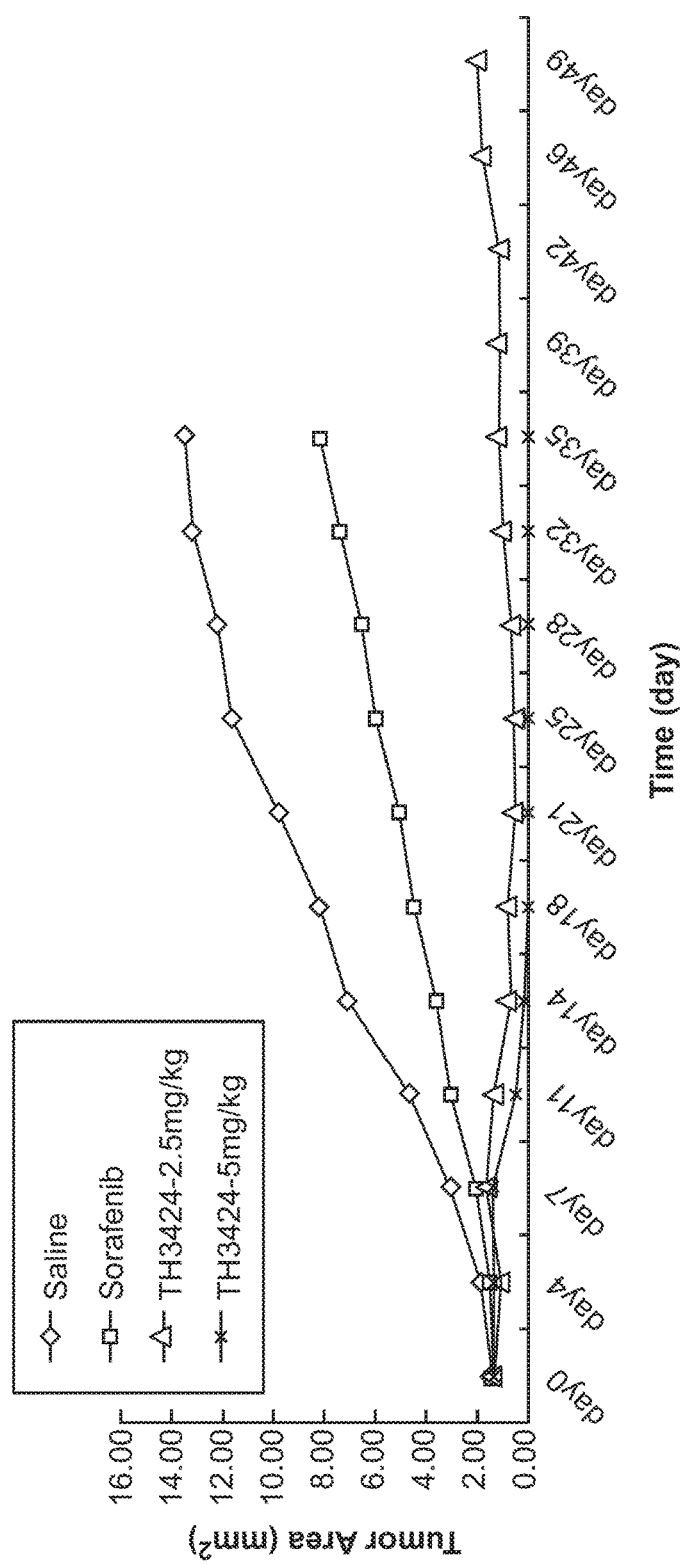
FIG. 7 illustrates tumor growth curves in each group.

The progressions of orthotopic HepG2-GFP hepatocellular carcinoma in different groups were monitored by real time imaging. Images were acquired twice a week. Typical tumor images at the end of the study in each group and tumor growth curves derived from the signals of tumor fluorescence, which were analyzed using the Power Station software (INDEC Biosystems, CA, USA), are shown in FIG. 6 and FIG. 7, respectively

TABLE

Average tumor size in each group (mm$^2$)

| Groups | Tumor area (mm$^2$) (mean ± sd) | P value |
|---|---|---|
| Saline (C) | 13.5 ± 2.7 | |
| Sorafenib (S) | 8.2 ± 5.3 | P = 0.0577 vs C; |
| TH3424 (2.5 mg/kg) | 1.2 ± 1.1 (Day 35) | P = 0.0000 vs C;<br>P = 0.0079 vs S |
|  | 2.0 ± 2.2 (Day 49) | P = 0.1163 vs TH3424 (2.5 mg/kg) (day 49) |
| TH3424 (5 mg/kg) | 0.0 ± 0.0 | P = 0.0000 vs C;<br>P = 0.0031 vs S<br>P = 0.0183 vs TH3424 (2.5 mg/kg) |

As shown in FIG. 6, FIG. 7 and the table above, the average tumor size in the positive control group was about 39% less than that in the negative control group, but there was no statistically significant difference between the 2 control groups (P=0.0577).

Figure 8:
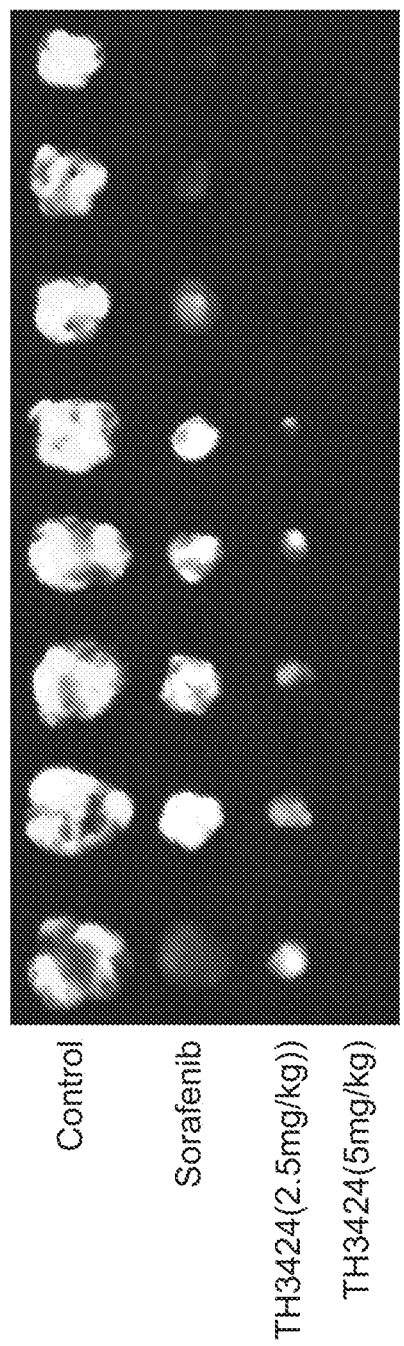
FIG. 8 illustrates fluorescence images of tumor burden in each group.
Figure 9:
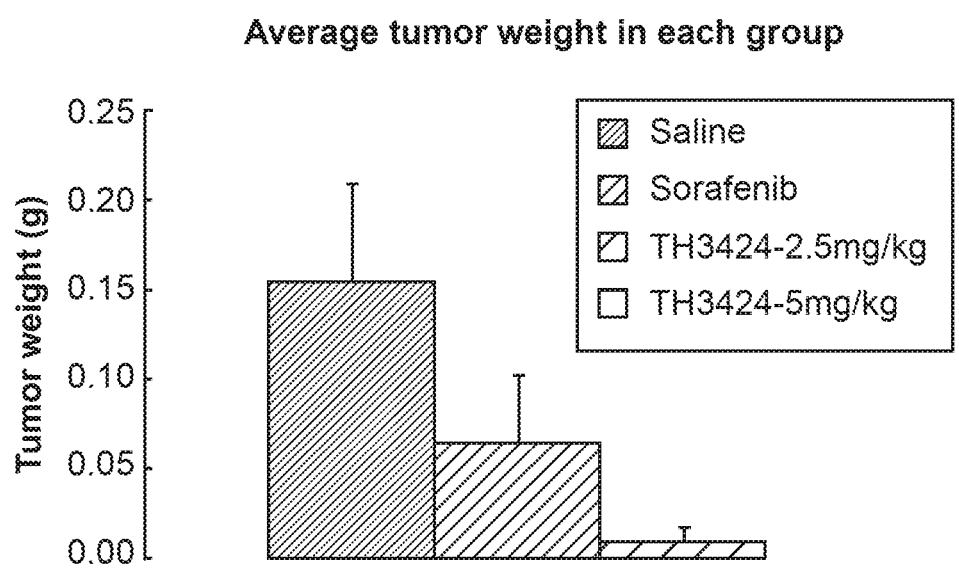
FIG. 9 illustrates average tumor weight in different groups.

In TH3424 (2.5 mg/kg) and TH3424 (5 mg/kg) groups, the average fluorescence imaging readout areas were significantly significant less than that in the negative control group, showing strong inhibitory effects and an obvious dose-effect relationship. Among them, the fluorescence imaging readout area was 0 in TH3424 (5 mg/kg) group. In this group, dosing was discontinued after 3 cycles of treatment; the tumor fluorescence imaging readout was still 0 until the end of experiment. In TH3424 (2.5 mg/kg) group, however, drug administration was stopped for 1 week after 3 cycles of treatment and then restarted another 3 cycles of treatment. The average fluorescence imaging readout area on day 35 was 1.2±1.1, which was around 8% of that in the negative control group and, it was 2.0±2.2 (~8%) of that in the negative control group on day 49 after treatment. FIG. 8 shows all tumors at the end of the study and FIG. 9 shows the average value of tumor weight in each of the experimental groups.

TABLE

Average tumor weight in each group

| Groups | Tumor weight (g) (mean ± sd) | P value |
|---|---|---|
| Saline (C) | 0.1543 ± 0.0546 | |
| Sorafenib (S) | 0.0637 ± 0.0389 | P = 0.0159 vs C |
| TH3424 (2.5 mg/kg) | 0.0081 ± 0.0088 (Day 49) | P = 0.0002 vs C;<br>P = 0.0020 vs S |
| TH3424 (5 mg/kg) | 0.0000 ± 0.0000 | P = 0.0001 vs C;<br>P = 0.0024 vs S;<br>P = 0.0341 vs TH3424 (2.5 mg/kg) |

As shown in FIG. 8, FIG. 9 and the table above, the average tumor weight of the positive control group was less than that of the negative control group (P=0.0159), which showed that the positive control drug (sorafenib) had inhibitory effect on orthotopic HepG2-GFP human hepatocellular carcinoma mouse model at the tested dosage.

The average tumor weight in group of TH3424 (2.5 mg/kg) and TH3424 (5 mg/kg) was 0.0081 g and 0 g, respectively. All was statistically significant less than that in the negative control group. Among them, the average weight was 0 g in the high dose group, and it was only 0.0081±0.0088 g in the low dose group, which was 0% and 5.2% of that in the negative control group, respectively. This suggested that TH3424 had a very strong inhibitory effect on orthotopic HepG2-GFP human hepatocellular carcinoma mouse model at tested dosages and it also showed a clear dose-effect relationship.

Tumor IR was calculated based on the final average tumor weights according to the formula:

IR (%)=(1−treatment(t)/control(c))×100

IR for each treatment group:

IR (%)=(1−PC/NC)×100=(1−0.0637/0.1543)× 100=58.7%

IR (%)=(1−TH2870-2LT/NC)×100=(1−0.0081/ 0.1543)×100=94.8%

IR (%)=(1−TH2870-2HT/NC)×100=(1−0.0000/ 0.1543)×100=100%

Note:
NC represents the negative control group
PC positive control group

The tumor inhibition rate was 58.7% in the sorafenib treated group (P=0.0159 vs control), showing strong inhibitory effect on orthotopic HepG2-GFP human hepatocellular carcinoma mouse model at the tested dosage. However, in this group, the average body weight of the experimental mice was statistically significant lower than that in the negative control group. It suggested that there was a certain degree of toxicity to the experimental mice by administration of sorafenib at the tested dosage. The tumor inhibition rate of TH3424 (2.5 mg/kg) and TH3424 (5 mg/kg) was 94.8% and 100%, respectively, showing a very strong tumor inhibitory effect and a clear dose-effect relationship on orthotopic HepG2-GFP human hepatocellular carcinoma mouse model. There was no obvious toxicity to the experimental mice at the tested dosages of TH3424

Example 10. TH3424 in T-Cell Leukemia Animal Models

Leukemic cells were prepared by thawing out ~150×106 of AL7473 cells from LN2 (about 2-3 vials) and placing them into a 37° C. water bath rapidly. All of the cells were transferred into a 50 ml falcon tube with 40 ml pre-warmed complete medium. The cells were centrifuged at 1200 rpm for 5 min. The cells were re-suspended with 40 ml RPMI1640. The cells were then counted. The cells were centrifuged at 1200 rpm for 5 min. and re-suspended with ice cold PBS to 2 million cell per 100 ul PBS. 100 ul of saline containing 2×106 cells prepared above were used to inject into each mouse by IV. The FACS analysis was done for blood weekly during the experimental period by transferring samples into FACS tubes, adding human CD45 FITC and isotypes into corresponding tubes for all the samples and incubating the cells on ice for 30 min. in the dark. 2 ml of red blood cell lysing buffer was added to each tube and incubated on ice for another 30 min. in the dark. All the samples were vortexed several times during this process and the samples were centrifuged for 5 min. at 1500 rpm at 4° C. The supernatants were discarded and 2 ml of ice cold wash buffer was added into each tube. The samples were centrifuged for 5 min at 1500 rpm at 4° C. and these steps were repeated. The cells were re-suspended into 150 µl of wash buffer/PBS for FACS acquisition. Samples were analyzed on a BD Calibur by using Cell Quest or Flowjo and the results were analyzed by using Prism 5.0.

Blood samples for FACS were collected at day 26, 33, 42 post cell inoculation pre-group. After the group samples, FACS was done weekly until the study was finished (Day 50, 57, 64 post cells inoculation). 10 µl plasma samples were collected for each mouse and 3 blood smears were done from each group (Group1: #7, #43, #52; Group2: #11, #15, #23; Group3: #5, #9, #48; Group4: #25, #28, #36) at day 57 post cell inoculation. The samples list is summarized below.

TABLE

Sample collection at termination point for all animals.

| Sample Source | Usage | Comments |
|---|---|---|
| Blood | FACS (human CD45) | All mice |
| Bone marrow | FACS (human CD45) | All mice |
|  | fixed in formalin, embedded in paraffin | 3 mice each group |
| Spleen | FACS (human CD45) | All mice |
|  | fixed in formalin, embedded in paraffin | 3 mice each group |

Figure 10:
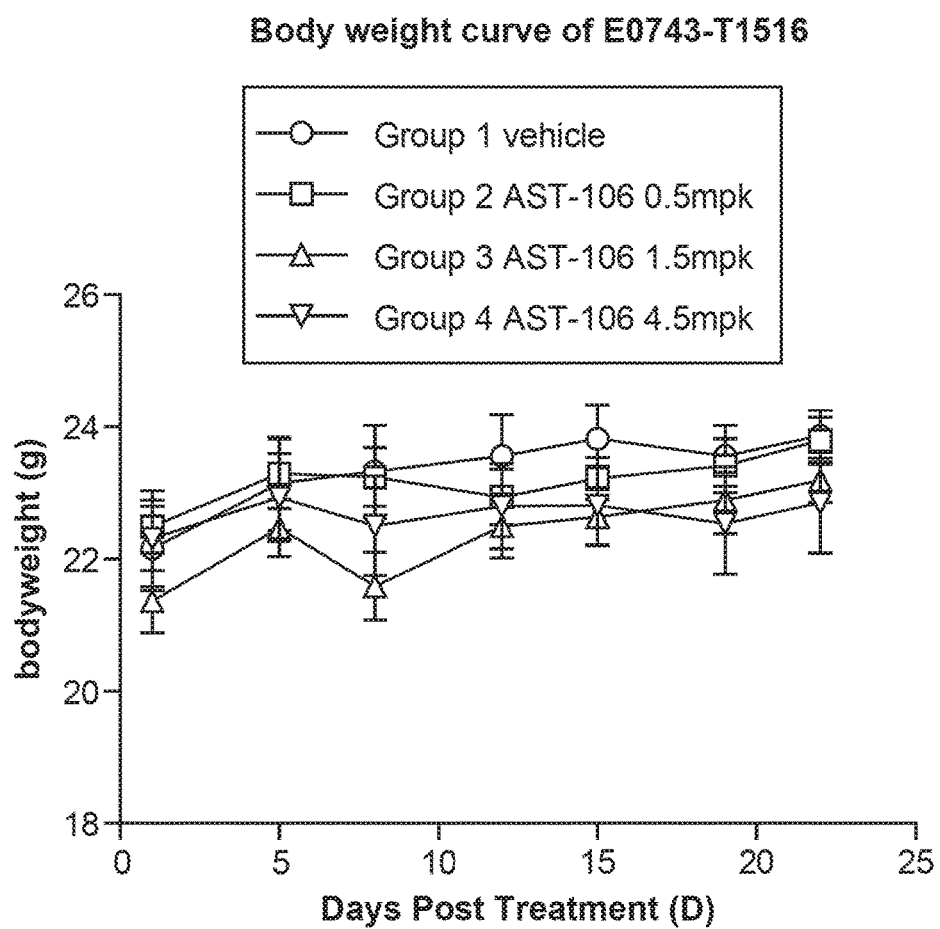
FIG. 10 illustrates body weight changes in different groups.
Figure 11:
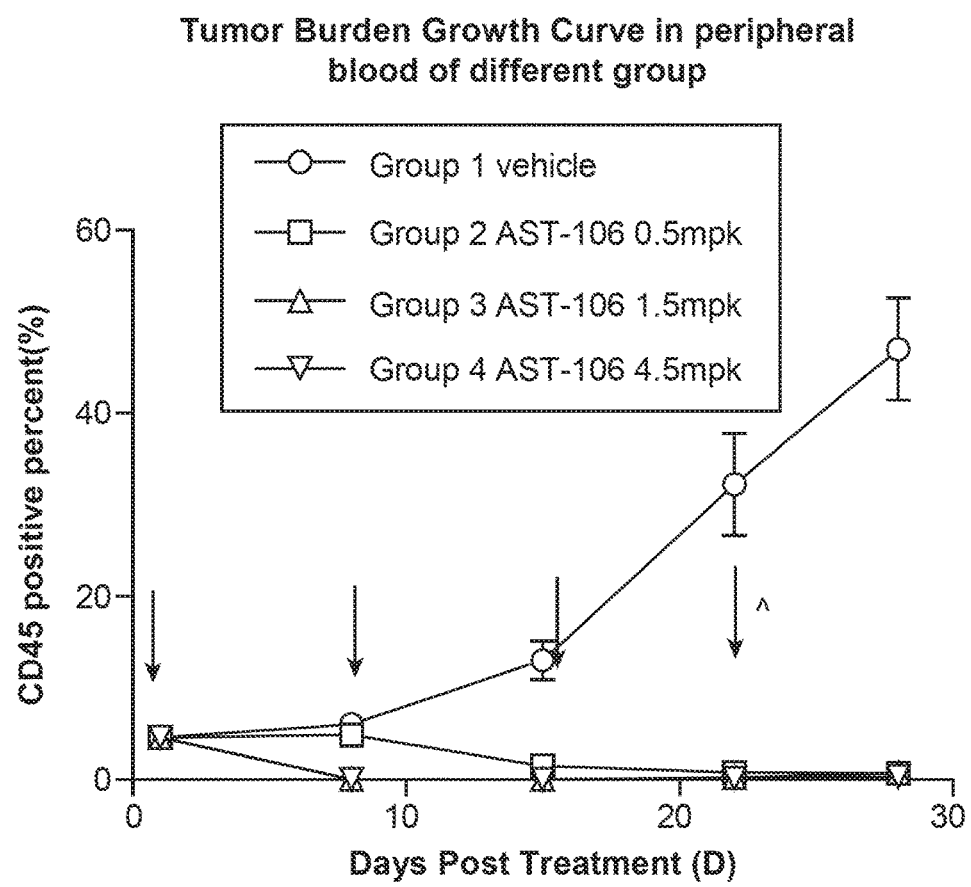
FIG. 11 illustrates the tumor burden growth curve in peripheral blood.
Figure 12:
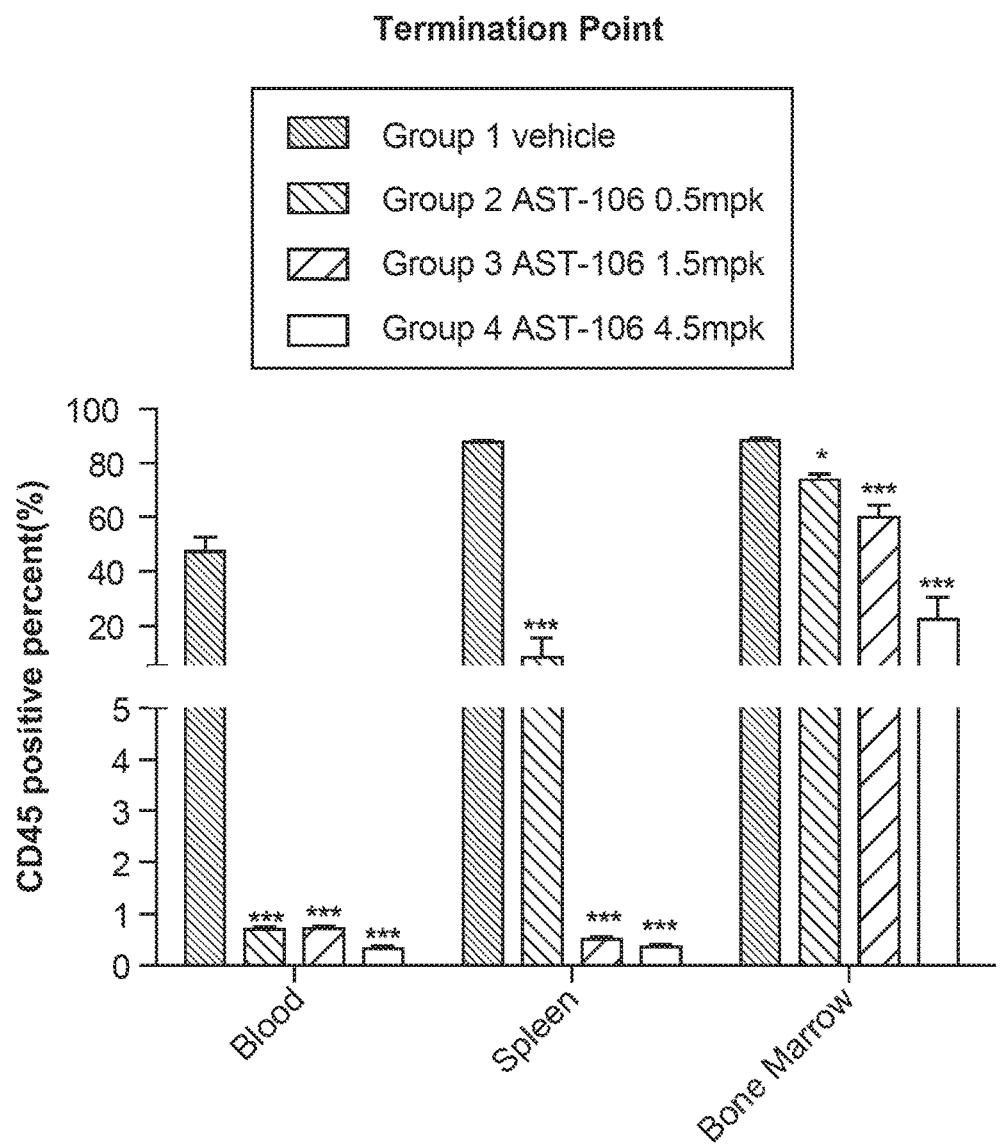
FIG. 12 illustrates the human CD45 antibody positive percent in blood, spleen and bone marrow at termination point in different groups.

The results of the body weights changes in the mice are shown in FIG. 10. Peripheral blood was collected weekly for human CD45 antibody FACS detected during treatment since the treatment start on Day 43 post cell inoculation. The mice were respectively dosed at Day 43, 50, 57 and 64 (only dosing group1 and group2) post cells inoculation. The tumor burden growth curve after grouping is shown in FIG. 11. The percentages of human CD45+ leukemia cells in peripheral blood of each group increased as disease progressed, and the percentage curves dropped at 7 days after the first dosing except group2 (P>0.05). After the second dosing, the treatment group (group2-4) were significantly lower than vehicle group (group1) (P<0.001). All mice (total of 4 groups, 10 mice in each group) were sacrificed at 6 days after the fourth dosing. Blood, spleen and bone marrow of all mice were collected for human CD45 FACS detected. Spleen and bone of 3 mice in each group were collected for FFPE. The detail data and samples list at termination point summarized in Appendix 10.3. The tumor burden in peripheral blood, spleen and bone marrow of mice at study termination point is shown in FIG. 12. Respectively compared to blood, spleen and bone marrow of group1, except bone marrow in group2 showed slightly significant differences (P<0.05), all treatment group (groups 2-4) showed significant differences (P<0.01).

Example 10. Pharmacokinetics and Acute Toxicity Study in No Naïve Monkeys

TH 3423 and TH 3424 were tested in no naïve monkeys (1 male and one female for each compound at 2 mg/kg) with 30-min intravenous infusion, TK sampling: on Day 1 and Day 15: 0.25, 0.5, 0.75, 1 and 2 hr post infusion initiation. Serum chemistry and hematology: pre-dose (Day 1), day 5, day 8 (pre-dose), day 15 (pre-dose), day 22 and day 28. Clinical observation: Daily during the study, total 35 days. Food consumption: Daily during the study, total 35 days. Bodyweight measurement: Twice weekly for five weeks.

The TK parameters are listed in the following tables:

Plasma concentration of TH3423 after 30-min IV infusion to male and female Cynomolgus monkeys at 2 mg/kg

| Dosage | Time points (hr) | concentration (ng/mL) | | Mean (ng/mL) |
|---|---|---|---|---|
|  |  | male_#1 | female_#2 |  |
| IV-TH3423 2 mg/kg | 0.25 | 1100 | 1320 | 1210 |
|  | 0.5 | 1420 | 1370 | 1395 |
|  | 0.75 | 359 | 313 | 336 |
|  | 1 | 85.0 | 55.0 | 70.0 |
|  | 2 | 1.03 | BQL | 1.03 |

| TK parameters | Unit | #1- | #2 | Mean |
|---|---|---|---|---|
| CL | L/hr/kg | 2.59 | 2.61 | 2.60 |
| $V_{ss}$ | L/kg | 0.584 | 0.469 | 0.5266 |
| $AUC_{last}$ | hr*ng/mL | 773 | 758 | 766 |
| $AUC_{INF}$ | hr*ng/mL | 774 | 766 | 770 |
| Terminal $t_{1/2}$ | hr | 0.150 | 0.108 | 0.129 |
| $MRT_{INF}$ | hr | 0.226 | 0.180 | 0.2028 |

Plasma concentration of TH3424 after 30-min IV infusion to male and female Cynomolgus monkeys at 2 mg/kg

| Dosage | Time points (hr) | concentration (ng/mL) male_#3 | female_#4 | Mean (ng/mL) |
|---|---|---|---|---|
| IV-TH3424 2 mg/kg | 0.25 | 2480 | 1850 | 2165 |
| | 0.5 | 2720 | 2090 | 2405 |
| | 0.75 | 1030 | 557 | 794 |
| | 1 | 260 | 110 | 185 |
| | 2 | 7.43 | 3.84 | 5.64 |

Plasma concentration of TH3424 after 30-min IV infusion to male and female Cynomolgus monkeys at 2 mg/kg

| TK parameters | Unit | #3 | #4 | Mean |
|---|---|---|---|---|
| CL | L/hr/kg | 1.16 | 1.67 | 1.42 |
| Vss | L/kg | 0.289 | 0.360 | 0.3246 |
| AUClast | hr*ng/mL | 1724 | 1195 | 1459 |
| AUCINF | hr*ng/mL | 1726 | 1196 | 1461 |
| Terminal t½ | hr | 0.181 | 0.182 | 0.182 |
| MRTINF | hr | 0.250 | 0.215 | 0.2324 |

The serum chemistry is shown in the following table:

| Gender | Animal ID | Time of sampling | ALT (U/L) | AST (U/L) | ALP (U/L) | γ-GT (U/L) | TBIL (μM) | TP (g/L) | ALB (g/L) | BUN (μM) | Glu (mM) |
|---|---|---|---|---|---|---|---|---|---|---|---|
| Group 1 TH3423 Male | #1 | Day 1 | 45.0 | 37.0 | 746.4 | 78.4 | 5.2 | 72.9 | 46.9 | 3.47 | 3.12 |
| | | Day 8 | 21.0 | 40.8 | 540.3 | 37.6 | 9.8 | 76.2 | 39.1 | 26.82 | 5.28 |
| Female | #2 | Day 1 | 41.7 | 43.3 | 205.5 | 41.5 | 0.0 | 66.0 | 42 | 4.06 | 6.03 |
| | | Day 8 | 25.5 | 57.7 | 190.3 | 37.0 | 0.4 | 71.8 | 40.9 | 7.61 | 2.13 |
| | | Day 15 | 21.1 | 76.7 | 123.6 | 29.4 | 1.4 | 54.9 | 34.2 | 5.96 | 2.51 |
| Group 2 TH3424 Male | #3 | Day 1 | 43.0 | 40.2 | 287.5 | 62.2 | 2.1 | 70.4 | 50.5 | 4.89 | 4.5 |
| | | Day 8 | 31.2 | 31.2 | 225.2 | 44.9 | 3.6 | 65.1 | 43.3 | 4.8 | 4.15 |
| | | Day 15 | 45.0 | 73.5 | 174.8 | 36.7 | 2.1 | 53.2 | 36.8 | 9.66 | 1.47 |
| Female | #4 | Day 1 | 61.6 | 23.7 | 134.2 | 47.3 | 1.5 | 70.2 | 46.1 | 3.43 | 3.34 |
| | | Day 8 | 37.7 | 43.1 | 200.2 | 36.2 | 0.8 | 72.4 | 41.8 | 5.63 | 5.91 |
| | | Day 15 | 31.9 | 23.8 | 151.5 | 34.2 | 4.0 | 62.3 | 38.5 | 3.87 | 2.8 |

| Gender | Animal ID | Time of sampling | TC (mM) | TG (mmol/L) | Ca (mmol/L) | P (mmol/L) | CK (U/L) | GLB (g/L) | CREA (μM) |
|---|---|---|---|---|---|---|---|---|---|
| Group 1 TH3423 Male | #1 | Day 1 | 2.1 | 0.24 | 2.54 | 1.27 | 146 | 26 | 66 |
| | | Day 8 | 1.72 | 2.25 | 2.55 | 1.84 | 153 | 37.1 | 141 |
| Female | #2 | Day 1 | 2.48 | 0.45 | 2.39 | 1.02 | 342 | 24 | 95 |
| | | Day 8 | 3.01 | 1.17 | 2.47 | 1.53 | 126 | 30.9 | 120 |
| | | Day 15 | 2.02 | 0.84 | 2.36 | 1.09 | 78 | 20.7 | 69 |
| Group 2 TH3424 Male | #3 | Day 1 | 3.22 | 0.38 | 2.38 | 1.66 | 221 | 19.9 | 91 |
| | | Day 8 | 3.06 | 0.66 | 2.33 | 1.57 | 83 | 21.8 | 96 |
| | | Day 15 | 1.44 | 0.41 | 2.14 | 1.5 | 172 | 16.4 | 58 |
| Female | #4 | Day 1 | 3.04 | 0.17 | 2.51 | 1.21 | 202 | 24.1 | 61 |
| | | Day 8 | 2.91 | 0.63 | 2.37 | 1.31 | 190 | 30.6 | 88 |
| | | Day 15 | 2.23 | 0.94 | 2.2 | 1.22 | 78 | 23.8 | 46 |

| Gender | Animal ID | Time of sampling | A/G | Na (mmol/L) | K (mmol/L) | Cl (mmol/L) |
|---|---|---|---|---|---|---|
| Group 1 TH3423 Male | #1 | Day 1 | 1.8 | 143 | 6.92 | 106 |
| | | Day 8 | 1.1 | 112 | 5.86 | 71.2 |
| Female | #2 | Day 1 | 1.8 | 146 | 6.14 | 104 |
| | | Day 8 | 1.3 | 149 | 4.83 | 97.9 |
| | | Day 15 | 1.7 | 128.17 | 4.81 | 83.87 |
| Group 2 TH3424 Male | #3 | Day 1 | 2.5 | 147 | 4.31 | 110 |
| | | Day 8 | 2.0 | 147 | 4.51 | 97.2 |
| | | Day 15 | 2.2 | 136.14 | 6.05 | 92.47 |
| Female | #4 | Day 1 | 1.9 | 143 | 5.77 | 108 |
| | | Day 8 | 1.4 | 143 | 4.33 | 97.1 |
| | | Day 15 | 1.6 | 132.59 | 5.58 | 95.29 |

The hematology data are shown in the following table:

| Gender | Animal ID | Time of sampling | WBC (×10⁹/L) | % NEUT (%) | LYM (%) | % MONO (%) | % EOS (%) | % BASO (%) | abs_neuts (×10⁹/L) | abs_lymphs (×10⁹/L) |
|---|---|---|---|---|---|---|---|---|---|---|
| Group 1 TH3423 Male | #1 | Day 1 | 5.33 | 55.4 | 36.7 | 5.5 | 2.4 | 0.0 | 2.96 | 1.95 |
| | | Day 8 | 11.66 | 80.9 | 15.4 | 0.0 | 3.0 | 0.7 | 9.44 | 1.79 |
| Female | #2 | Day 1 | 6.7 | 47.9 | 45 | 4.8 | 2.3 | 0.0 | 3.21 | 3.02 |
| | | Day 8 | 10.35 | 61.90 | 35.60 | 0.00 | 2.30 | 0.20 | 6.40 | 3.68 |
| | | Day 15 | 9.56 | 63.0 | 27.90 | 6.30 | 2.70 | 0.10 | 6.02 | 2.67 |

-continued

| | Gender | Animal ID | Time of sampling | | | | | | | | |
|---|---|---|---|---|---|---|---|---|---|---|---|
| Group 2 TH3424 | Male | #3 | Day 1 | 4.71 | 58.4 | 38.9 | 0.1 | 2.6 | 0.0 | 2.75 | 1.84 |
| | | | Day 8 | 9.15 | 34.60 | 45.90 | 13.10 | 1.10 | 5.30 | 3.16 | 4.19 |
| | | | Day 15 | 13.26 | 65.7 | 26.70 | 4.40 | 3.10 | 0.10 | 8.70 | 3.54 |
| | Female | #4 | Day 1 | 11.64 | 72.8 | 22.9 | 0.9 | 3.3 | 0.1 | 8.47 | 2.66 |
| | | | Day 8 | 16.91 | 49.10 | 18.90 | 0.20 | 1.50 | 30.30 | 8.29 | 3.20 |
| | | | Day 15 | 20.70 | 80.8 | 13.60 | 3.00 | 1.70 | 0.90 | 16.7 | 2.80 |

| | Gender | Animal ID | Time of sampling | abs_monos (×10⁹/L) | abs_eos (×10⁹/L) | abs_basos (×10⁹/L) | RBC (×10¹²/L) | HGB (g/L) | HCT (%) | MCV (fL) | MCH (pg) |
|---|---|---|---|---|---|---|---|---|---|---|---|
| Group 1 TH3423 | Male | #1 | Day 1 | 0.29 | 0.13 | 0.0 | 5.2 | 132 | 40.8 | 78.3 | 25.4 |
| | | | Day 8 | 0.00 | 0.35 | 0.08 | 5.86 | 146.00 | 44.70 | 76.20 | 24.90 |
| | Female | #2 | Day 1 | 0.32 | 0.15 | 0 | 4.67 | 112 | 35 | 74.9 | 24 |
| | | | Day 8 | 0.00 | 0.25 | 0.02 | 5.21 | 128.00 | 39.80 | 76.30 | 24.60 |
| | | | Day 15 | 0.60 | 0.26 | 0.01 | 4.8 | 115 | 33.9 | 70.6 | 24.0 |
| Group 2 TH3424 | Male | #3 | Day 1 | 0 | 0.12 | 0 | 4.55 | 117 | 34.9 | 76.7 | 25.7 |
| | | | Day 8 | 1.21 | 0.10 | 0.49 | 4.59 | 117.00 | 35.20 | 76.70 | 25.50 |
| | | | Day 15 | 0.59 | 0.41 | 0.02 | 5.02 | 127 | 37.4 | 74.5 | 25.3 |
| | Female | #4 | Day 1 | 0.11 | 0.39 | 0.01 | 4.65 | 118 | 35.7 | 76.8 | 25.4 |
| | | | Day 8 | 0.03 | 0.26 | 5.13 | 5.15 | 130.00 | 39.30 | 76.30 | 25.30 |
| | | | Day 15 | 0.62 | 0.37 | 0.19 | 4.94 | 125 | 36.3 | 73.5 | 25.3 |

| | Gender | Animal ID | Time of sampling | MCHC (g/L) | RDW-CV (%) | RDW-SD (fL) | PLT (×10⁹/L) | MPV (fL) | PDW | PCT (%) |
|---|---|---|---|---|---|---|---|---|---|---|
| Group 1 TH3423 | Male | #1 | Day 1 | 324 | 11.6 | 38.2 | 358 | 10.2 | 15.1 | 0.365 |
| | | | Day 8 | 327.00 | 11.90 | 38.00 | 490.00 | 10.60 | 15.70 | 0.52 |
| | Female | #2 | Day 1 | 320 | 11.8 | 37.2 | 318 | 10.6 | 14.8 | 0.338 |
| | | | Day 8 | 322.00 | 12.30 | 39.50 | 699.00 | 9.60 | 15.40 | 0.67 |
| | | | Day 15 | 339 | 10.9 | 32.3 | 533 | 8.70 | 15.10 | 0.46 |
| Group 2 TH3424 | Male | #3 | Day 1 | 335 | 11.8 | 38.1 | 240 | 11.1 | 15.5 | 0.267 |
| | | | Day 8 | 332.00 | 11.50 | 37.20 | 496.00 | 10.30 | 15.30 | 0.51 |
| | | | Day 15 | 340 | 11.5 | 36.3 | 623 | 9.5 | 15.4 | 0.593 |
| | Female | #4 | Day 1 | 331 | 11.5 | 37.4 | 213 | 13 | 15.4 | 0.277 |
| | | | Day 8 | 331.00 | 11.20 | 36.20 | 390.00 | 12.80 | 15.50 | 0.50 |
| | | | Day 15 | 344 | 11.0 | 34.1 | 221 | 12.5 | 16.2 | 0.275 |

The body weight changes are listed in the following table:

| Group No. | Animal ID | Day 1 | Day 4 | Day 8 | Day 11 |
|---|---|---|---|---|---|
| Group 1 TH3423 | #1 | 3.35 | 3.23 | 3.23 | 2.95 |
| | #2 | 3.65 | 3.55 | 3.41 | 2.96 |
| | Mean | 3.50 | 3.39 | 3.32 | 2.96 |
| Group 2 TH3424 | #3- | 3.40 | 3.30 | 3.31 | 3.17 |
| | #4 | 3.28 | 3.22 | 3.08 | 2.94 |
| | Mean | 3.34 | 3.26 | 3.20 | 3.06 |

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:

1. The compound (R)-1-(3-(3-N,N-dimethylaminocarbonyl)phenoxyl-4-nitrophenyl)-1-ethyl-N,N'-bis(ethylene) phosphoramidate:

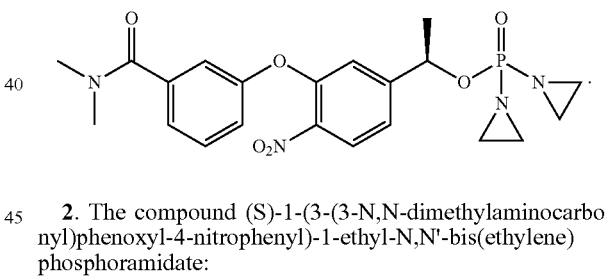

2. The compound (S)-1-(3-(3-N,N-dimethylaminocarbonyl)phenoxyl-4-nitrophenyl)-1-ethyl-N,N'-bis(ethylene) phosphoramidate:

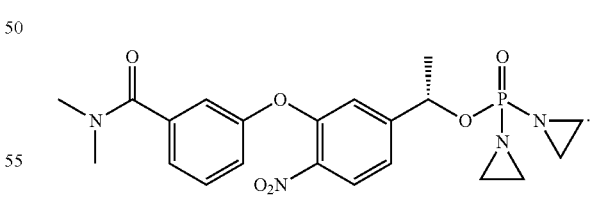

3. The compound of claim 1, wherein the compound has an enantiomeric excess of no less than 80%.

4. The compound of claim 3, wherein the compound has an enantiomeric excess of no less than 90%.

5. The compound of claim 4, wherein the compound has an enantiomeric excess of no less than 95%.

6. The compound of claim 1, wherein the compound is substantially pure.

7. The compound of claim 6, wherein the compound has a purity of at least 50%.

8. The compound of claim 7, wherein the compound has a purity of at least 90%.

9. A pharmaceutical composition comprising the compound of claim 1, and a pharmaceutically acceptable excipient.

10. A method of treating, or ameliorating one or more symptoms of a proliferative disease in a subject, comprising administering to the subject a compound of claim 1.

11. The method of claim 10, wherein the disease is cancer including liver cancer, hepatocellular carcinoma (HCC), non-small cell lung cancer, melanoma, prostate cancer, breast cancer, leukemia, esophageal cancer, renal cancer, gastric cancer, colon cancer, brain cancer, bladder cancer, cervical cancer, ovarian cancer, head and neck cancer, endometrial cancer, pancreatic cancer, a sarcoma cancer, and rectal cancer.

12. A method of inhibiting the growth of a cell, comprising contacting the cell with a compound of claim 1.

13. The method of claim 12, wherein the cell is a cancerous cell.

14. A process of making the compound of formula I:

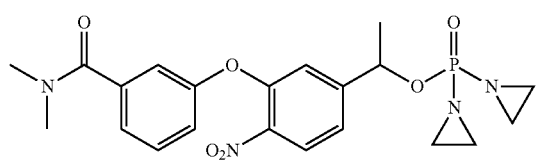

I comprising contacting a compound of formula II:

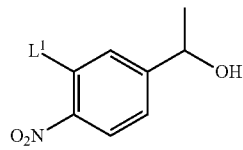

II with $POCl_3$ and $H_2NCH_2CH_2L^2$ or a salt thereof, to provide a compound of formula III,

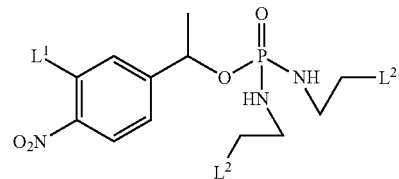

III wherein $L^1$ and $L^2$, independently are a leaving group, and converting the compound of formula III to a compound of formula I, $MeSO_3$.

15. A process for the resolution into one of the enantiomers of the racemate of the compound of claim 1 or for the enrichment of a mixture with any enantiomeric excess of said compound of formula (I), comprising the following steps: a) subjecting the compound of formula (I): to an optical resolution process wherein a racemic enantiomerically enriched mixture of 1-(3-(3-N,N-dimethylaminocarbonyl)phenoxyl-4-nitrophenyl)-1-ethyl-N,N'-bis(ethylene) phosphoramidate is separated into its two enantiomers (S)-1-(3-(3-N,N-dimethylaminocarbonyl)phenoxyl-4-nitrophenyl)-1-ethyl-N,N'-bis(ethylene)phosphoramidate and (R)-1-(3-(3-N,N-dimethylaminocarbonyl)phenoxyl-4-nitrophenyl)-1-ethyl-N,N'-bis(ethylene)phosphoramidate by chiral chromatography comprising a stationary phase and a mobile phase, wherein the stationary phase comprises a silica gel impregnated with a functionalized polysaccharide, and wherein the mobile phase comprises an alcohol and another solvent.

16. The process of claim 15, wherein the alcohol is methanol.

17. The process of claim 15, wherein the another solvent is $CO_2$.

18. A pharmaceutical composition comprising the compound of claim 2, and a pharmaceutically acceptable excipient.

19. A method of treating, or ameliorating one or more symptoms of a proliferative disease in a subject, comprising administering to the subject a compound of claim 2.

20. A method of inhibiting the growth of a cell, comprising contacting the cell with a compound of claim 2.

* * * * *